United States Patent [19]
Freidinger et al.

[11] Patent Number: 5,206,237
[45] Date of Patent: Apr. 27, 1993

[54] BENZODIAZEPINE ANALOGS

[75] Inventors: Roger M. Freidinger, Lansdale; Mark G. Bock, Hatfield; Ben E. Evans, Lansdale, all of Pa.

[73] Assignee: Merck & Co., Inc., Rahway, N.J.

[21] Appl. No.: 699,849

[22] Filed: May 14, 1991

[51] Int. Cl.$^5$ .............................................. A61U 31/55
[52] U.S. Cl. .................................... 514/219; 514/221
[58] Field of Search ........................ 514/219, 222, 221

[56]  References Cited
U.S. PATENT DOCUMENTS

| | | |
|---|---|---|
| 852,478 | 3/1892 | Freidinger et al. .................. 514/221 |
| 4,755,508 | 3/1988 | Freidinger et al. .................. 514/221 |
| 4,820,834 | 4/1989 | Evan et al. ........................... 514/221 |

FOREIGN PATENT DOCUMENTS

| | | |
|---|---|---|
| 167920 | 1/1986 | European Pat. Off. |
| 280472 | 8/1988 | European Pat. Off. |
| 411668 | 2/1991 | European Pat. Off. |
| 90/11773 | 4/1989 | World Int. Prop. O. |

OTHER PUBLICATIONS

Bradwejn, et al., *Enhanced Sensitivity to Cholecystokinin Tetrapeptide in Panic Disorder*, Soc. Neurosci. Abstr. 14(1), p. 291, (1988).
de Montigny, *Cholecystokinin Tetrapeptide Induces Panic Attacks in Healthy Volunteers*, soc. Neurosci. Abstr. 14(1), p. 291, (1988).
Bradwejn, et al., *Benzodiazepines Antagonize Cholecystokinin—Induced Activation of Rat. Hippocampal*, Nature 312, p. 22, (1984).
de Montigny, *Cholecystokinin Tetrapeptide Induces Panic-Like Attacks in Healthy Volunteers*, Arch. Gen. Psychiatry, 46, (1989).
Dourish, et al., *Morphine Induced Analgesia in the rat Paw Pressure Test is Blocked by CCK and Enhanced by the CCK Antagonist MK-329*, Eur. Jour. Pharm. 147, No. 3, pp. 469–472, (1988).
Bouthillier, et al., *Long-term Benzodiazepine Treatment Reduces Neuronal Responsiveness to Cholecystokinin: an Electrophysiological Study in the Rat,* Eur. Jour. Pharm. 151, No. 1, pp. 135–138, (1988).
M. A. Silverman, *Cholecystokinin Receptor Antagonists: A Review* Amer. Mour. Gast., vol. 82, pp. 703–708 (1987).

*Primary Examiner*—S. J. Friedman
*Attorney, Agent, or Firm*—Mark R. Daniel; Joseph F. DiPrima

[57] ABSTRACT

Pharmaceutical compositions containing benzodiazepines of the formula:

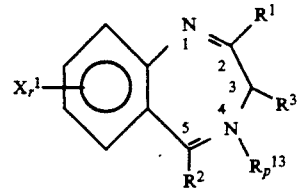

are disclosed which are useful in the treatment of panic disorder or anxiety disorder.

3 Claims, No Drawings

BENZODIAZEPINE ANALOGS

BACKGROUND OF THE INVENTION

The benzodiazepines (Formula IV) which are the starting materials for the compounds of Formula I are described in Merck U.S. Pat. No. 4,755,508.

Cholecystokinins (CCK) and gastrin are structurally-related neuropeptides which exist in gastrointestinal tissue and in the central nervous system (see, V. Mutt, *Gastrointestinal Hormones*, G. B. J. Glass, Ed., Raven Press, N.Y., p. 169 and G. Nisson, ibid, p. 127).

The isolation of the 33-amino acid polypeptide, cholecystokinin (CCK-33), from porcine intestine, Mutt, V. et al., "Structure of Porcine Cholecystokininpancreozymin. 1. Cleavage with Thrombin and Trypsin", *European J. Biochem.* 6, 156, (1968), was followed by the discovery that it occurs in numerous molecular forms at various sites throughout the peripheral and central nervous systems, Larsson, L. et al., "Localization and Molecular Heterogeneity of Cholecystokinin in the Central and Peripheral Nervous System", *Brain Res.*, 165, 201 (1979). In the mammalian brain the predominant fragments are the carboxy terminal octapeptide, H-Asp-Tyr($SO_3H$)-Met-Gly-Trp-Met-Asp-Phe-$NH_2$ (CCK-8s, $CCK_{26-33}$) and tetrapeptide, CCK-4 ($CCK_{30-33}$).

The carboxy terminal octapeptide possesses the full biological profile of CCK, Dockray, G. J. et al., "Isolation, Structure and Biological Activity of Two Cholecystokinin Octapeptides from Sheep Brain", *Nature* 274, 711 (1978), and meets many anatomical and biochemical criteria which characterize a neurotransmitter, Vanderhaeghen, J. J. et al., "J. Neuronal Cholecystokinin", *Ann. N.Y. Acad. Sci.*, 448, (1985). The presence of high concentrations of CCK-8s in the mammalian CNS is complemented with findings of specific and high affinity membrane-bound CCK binding sites, Innis, R. B. et al., "Distinct Cholecystokinin Receptors in Brain and Pancreas", *Proc. Natl. Acad. Sci. U.S.A.*, 77, 6917 (1980).

Evidence that more than one form of CCK receptor might exist was first provided in 1980 by Innis and Snyder, Innis, R. B. et al., "Distinct Cholecystokinin Receptors in Brain and Pancreas", *Proc. Natl. Acad. Sci. U.S.A.*, 77, 6917 (1980). At present, CCK receptors have been differentiated into primarily two subtypes based on their affinity for CCK fragments and analogues, Innis, R. B. et al., "Distinct Cholecystokinin Receptors in Brain and Pancreas", *Proc. Natl. Acad. Sci. U.S.A.*, 77, 6917 (1980). The subsequent development of agents which discriminate between different CCK receptor types afforded further support for these assignments, Chang, R. S. L. et al., "Biochemical and Pharmacological Characterization of an Extremely Potent and Selective Nonpeptide Cholecystokinin Antagonist", *Proc. Natl. Acad. Sci. U.S.A.*, 83, 4923 (1986).

The CCK-A receptors, previously known as peripheral CCK receptors, are located in organs such as the pancreas, gallbladder, and colon. They exhibit high affinity for CCK-8s and a lower affinity for the corresponding desulphated fragment, CCK-8d, for CCK-4, and gastrin. Recent autoradiographic results have localized CCK-A receptors in the brain as well, Hill, D. R. et al., "Autoradiographic Localization and Biochemical Characterization of Peripheral Type CCK Receptors in Rat CNS Using Highly Selective Nonpeptide CCK Antagonists", *J. Neurosci.*, 7, 2967 (1987).

The majority of the CCK receptors in the brain are of the CCK-B type. These were previously designated as central CCK receptors. CCK-B receptors are widely distributed throughout the brain and display high affinity for CCK-8s, CCK-4, and pentagastrin, Hill, D. R. et al., "Autoradiographic Localization and Biochemical Characterization of Peripheral Type CCK Receptors in Rat CNS Using Highly Selective Nonpeptide CCK Antagonists", *J. Neurosci.*, 7, 2967 (1987).

In addition to the above mentioned CCK receptor subtypes is a third type, the stomach gastrin receptor, which appears to be closely related to the CCK-B receptor subtype, Beinfeld, M. C., "Cholecystokinin in the Central Nervous System; a Minireview", *Neuropeptides*, 3, 4111 (1983). The minimum fully potent CCK sequence at this receptor is CCK-4, Gregory, R. A., "A Review of some Recent Development in the Chemistry of the Gastrins", *Biorg. Chem.*, 8, 497 (1979).

A wide range of physiological responses has been attributed to CCK. In an effort to elucidate its biological roles, researchers have relied primarily on a collection of CCK-A antagonists which has been steadily supplemented and improved to now include very selective, high-affinity agents, Evans, B. E., "Recent Developments in Cholecystokinin Antagonist Research," *Drugs Future*, 14, 971 (1989). In addition to their value as investigative tools, CCK antagonists retain considerable therapeutic potential, Gertz, B. J., "Potential Clinical Applications, of a CCK Antagonist in Cholecystokinin Antagonists," Alan R. Liss, Inc.: New York, pp. 327 (1988).

In recent years, interest in agonists and antagonists of CCK has been stimulated by the possible clinical application of such compounds, Silverman, M. A. et al., "Cholecystokinin Receptor Antagonists, a Review", *Am. J. Gastroenterol*, 82, 703, (1987). The discovery of the presence of CCK in the brain and its significance in relation to its modulation of dopaminergic functions, effects on satiety, its roles in nociception, in anxiety, and other brain functions, Vanderhaeghen, J. J., et al., "J. Neuronal Cholecystokinin", *Ann. N.Y. Acad. Sci.* 448 (1985) has understandably intensified the search for CCK-B selective agents. Since the relevant biologically active fragment, CCK-8s, has a half-life of less than 1 hour, Deschodt-Lanckman, K., et al., "Degradation of Cholecystokinin-like Peptides by a Crude Rat Brain Synaptosomal Fraction: a Study by High Pressure Liquid Chromatography", *Reg. Pept.*, 2, 15 (1981), implicit in the development of candidates for clinical use are criteria of high potency, selectivity, long in-vivo duration, oral bioavailability, and capability of penetrating the blood-brain barrier. These are strict prerequisites, given the tenuous stature of peptides as drugs, Veber, D. F., et al., "The Design of Metabolically-stable Peptide Analogs", *Trends Neurosci.* 8, 392 (1985).

Nevertheless, by employing stratagems which stabilize peptide structures, advances have been made toward developing highly potent and selective peptidal CCK-B receptor ligands Charpentier, B. et al., "Cyclic Cholecystokinin Analogues with High Selectivity for Central Receptors". *Proc. Natl. Acad. Sci. U.S.A.*, 85, 1968, (1988). Analogues are now available which have proven resistant to enzymatic degradation Charpentier, B. et al., "Enzyme-resistant CCK Analogs with High Affinities for Central Receptors", *Peptides*, 9 835 (1988). Despite favorable receptor binding profiles, this class of compounds fails to meet previously cited key requirements which characterize a drug candidate. In response, researchers have turned to non-peptide compounds which offer a broader range of structure and physicochemical properties.

It was, therefore, an object of this invention to identify pharmaceutical compositions containing the compounds of Formula I which are useful in the treatment of panic disorder or anxiety disorder in a mammal, especially a human. The compounds of Formula I are also useful in the treatment of oncologic disorders, controlling pupil constriction in the eye, treating pain or inducing analgesia, or treating a withdrawal response produced by treatment or abuse of drugs or alcohol.

SUMMARY OF THE INVENTION

It has now been found that pharmaceutical compositions containing compounds of Formula I are useful in the treatment of panic disorder or anxiety disorder in a mammal, especially in a human. The compounds of Formula I are also useful in the treatment of oncologic disorders, controlling pupil constriction in the eye, treating pain or inducing analgesia, or treating a withdrawal response produced by treatment or abuse of drugs or alcohol.

DETAILED DESCRIPTION OF THE INVENTION

The pharmaceutical compositions of this invention contain compounds of Formula I:

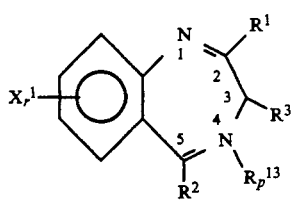

wherein $R^1$ is $-NR^{16}R^{17}$;

$R^2$ is H, loweralkyl, substituted or unsubstituted phenyl (wherein the substituents are 1 or 2 of halo, loweralkyl, loweralkoxy, loweralkylthio, carboxyl, carboxyloweralkyl, nitro, $-CF_3$, or hydroxy), 2-, 3-, 4-pyridyl, $-X^{12}COOR^6$,

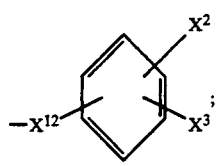

$R^3$ is $-X^{11}R^7$,

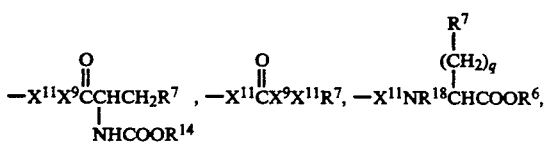

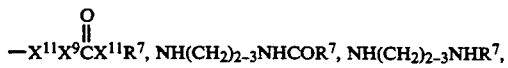

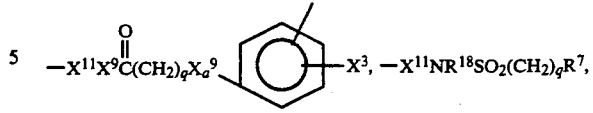

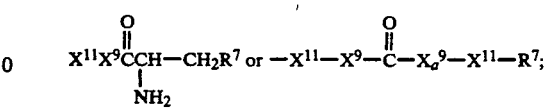

$R^4$ and $R^5$ are independently $R^6$ or in combination with the N of the $NR^4R^5$ group form an unsubstituted or mono or disubstituted, saturated or unsaturated, 4–7 membered heterocyclic ring, or benzofused 4–7 membered heterocyclic ring or said heterocyclic ring or said benzofused heterocyclic ring which further comprises a second heteroatom selected from O and $NCH_3$ and the substituent(s) is/are independently selected from $C_{1-4}$alkyl;

$R^6$ is H, loweralkyl, cycloloweralkyl, substituted or unsubstituted phenyl, or substituted or unsubstituted phenylloweralkyl (wherein the substituents are 1 or 2 of halo, loweralkyl, loweralkoxy, nitro, or $CF_3$);

$R^7$ is $\alpha$- or $\beta$-naphthyl, substituted or unsubstituted phenyl (wherein the substituents are 1 to 2 of halo, $-NO_2$, $-OH$, $-X^{11}-NR^4R^5$, loweralkyl, loweralkoxy, $CF_3$), loweralkylthio, cyano, phenyl, acetylamino, acetoxy, $SCF_3$, $C\equiv CH$, $CH_2SCF_3$, $OCHF_2$,

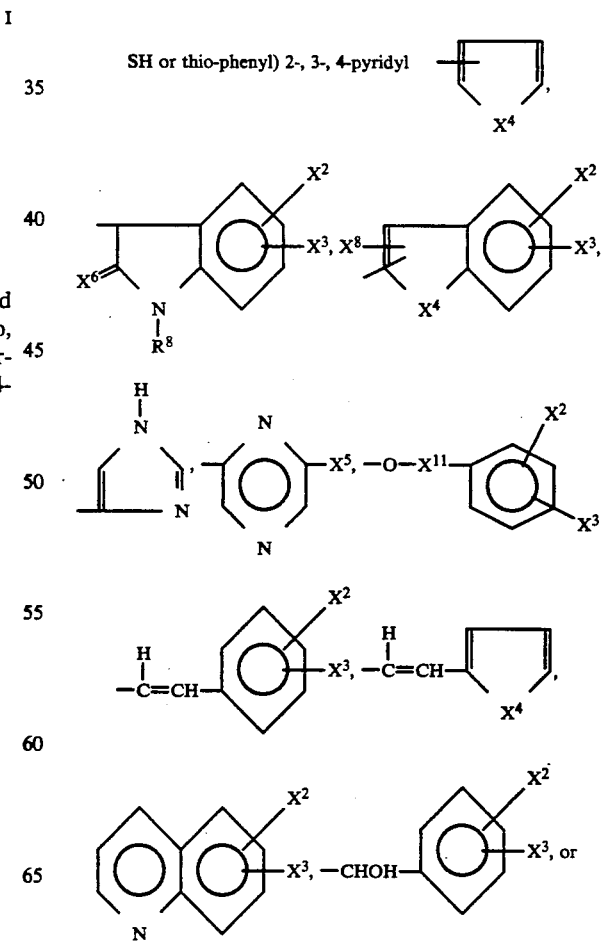

-continued

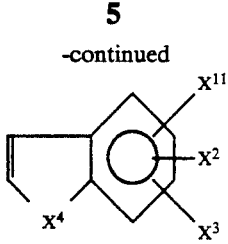

with the proviso that q is not O in

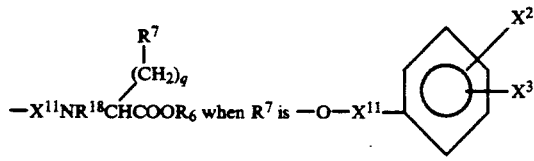

$R^8$ is H, loweralkyl, cycloloweralkyl, $-X^{12}CONH_2$, $-X^{12}COOR^6$, $-X^{11}$-cycloloweralkyl, $-X^{12}NR^4R^5$,

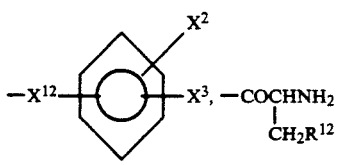

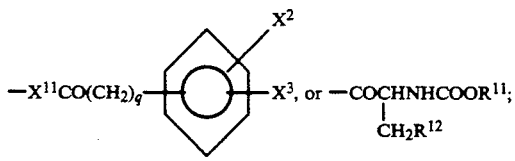

$R^{11}$ and $R^{12}$ are independently loweralkyl or cycloloweralkyl;
$R^{13}$ is O;
$R^{14}$ is loweralkyl or phenylloweralkyl;
$R^{16}$ and $R^{17}$ are, when separate, independently H, loweralkyl, lower alkenyl, $-X^{11}$cycloloweralkyl, $-X^{12}-NR^4R^5, X^{12}CONR^4R^5, -X^{12}C\equiv N$,

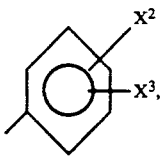

$-X^{12}COOR^6$, or $-CN$; or, when joined, form with N, a heterocycle

wherein n' is 2-6;
$R^{18}$ is H or loweralkyl;
p is 0 or 1;
q is 0-4;
r is 1 or 2;
$X^1$ is H, $-NO_2$, $CF_3$ CN, OH, loweralkyl, halo, loweralkylthio, loweralkoxy, $-X^{11}COOR^6$ or $-X^{11}NR^4R^5$;

$X^2$ and $X^3$ are independently H, $-OH$, $-NO_2$, halo, loweralkylthio, loweralkyl or loweralkoxy;
$X^4$ is S, O, $CH_2$ or $NR^8$;
$X^5$ is H, $CF_3$, CN, $COOR^6$, $NO_2$, or halo;
$X^6$ is O or HH;
$X^8$ is H or loweralkyl;
$X^9$ and $X^9_a$ are independently $NR^{18}$, O;
$X^{11}$ is absent or $C_{1-4}$ linear or branched alkylidene;
$X^{12}$ is $C_{1-4}$ linear or branched alkylidene; or a pharmaceutically acceptable salt thereof, and a pharmaceutically acceptable carrier.

In the compounds of Formula I, the preferred stereochemistry for CCK-A receptor antagonism relates to D-tryptophan, where $C^2$ and $N^4$ of Formula I correspond to the carbonyl carbon and α-amino nitrogen of D-tryptophan and $R^3$ occupies the position of the indolylmethyl side chain. For CCK-B and gastrin receptor antagonism, the preferred stereo-chemistry relates to L-tryptophan.

As used herein, the definition of each expression, e.g. p, loweralkyl, etc., when it occurs more than once in any structure, is intended to be independent of its definition elsewhere in the same structure.

As used herein, halo is F, Cl, Br or I; loweralkyl is 1-6 carbon straight or branched chain alkyl and includes methyl, ethyl, propyl, isopropyl, butyl, isobutyl, t-butyl, pentyl, and hexyl; in loweralkoxy and loweralkylthio, the alkyl portion is loweralkyl as previously defined; cycloloweralkyl is cycloalkyl of 3-5 carbons; and acyl is formyl, acetyl, propionyl, or butyryl.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

The pharmaceutically acceptable salts of the acid of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

An embodiment of this invention is the preparation of compounds of Formula I.

The compounds of Formula I may further be useful in the treatment or prevention of central nervous system disorders including neurological and pyschiatric disorders. Examples of such central nervous system disorders include anxiety disorders and panic disorders. Additional examples of central nervous system disorders include panic syndrome, anticipatory anxiety, phobic anxiety, panic anxiety, chronic anxiety, and endogenous anxiety.

The compounds of Formula I may further be useful in the treatment of oncologic disorders. Examples of such oncologic disorders include small cell adenocarcinomas and primary tumors of the central nervous system glial and neuronal cells. Examples of such adenocarcinomas and tumors include, but are not limited to, tumors of the lower esophagus, stomach, intestine, colon and lung, including small cell lung carcinoma.

The compounds of Formula I may further be used to control pupil constriction in the eye. The compounds may be used for therapeutic purposes during eye examinations and intraocular surgery in order to prevent miosis. The compounds may further be used to inhibit miosis occurring in association with iritis, uveitis and trauma.

The compounds of Formula I are also useful for directly inducing analgesia, opiate or non-opiate mediated, as well as anesthesia or loss of the sensation of pain.

The compounds of Formula I may further be useful for preventing or treating the withdrawal response produced by chronic treatment or abuse of drugs or alcohol. Such drugs include, but are not limited to cocaine, alcohol or nicotine.

A further embodiment is a composition comprising an effective amount of a compound of Formula I and a pharmaceutically acceptable carrier.

The compounds of Formula I thereof, may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight administered in single or divided doses.

In some cases, however, it may be necessary to use dosage levels outside these limits. For example, doses as low as about 1 ng/kg, about 0.005 μg to about 0.05 μg, or about 100 ng to about 100 μg/kg may be administered.

In the effective treatment of panic syndrome, panic disorder, anxiety disorder and the like, preferably about 0.05 mg/kg to about 0.5 mg/kg of CCK antagonist maybe administered orally (p.o.), administered in single or divided doses per day (b.i.d.). Other routes of administration are also suitable.

For directly inducing analgesia, anesthesia or loss of pain sensation, the effective dosage range is preferably from about 100 ng/kg to about 1 mg/kg by intraperitoneal administration. Oral administration is an alternative route, as well as others.

The compounds of Formula I are prepared according to the following scheme.

REACTION SCHEME I

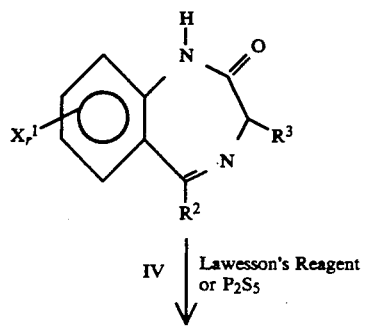

REACTION SCHEME I -continued

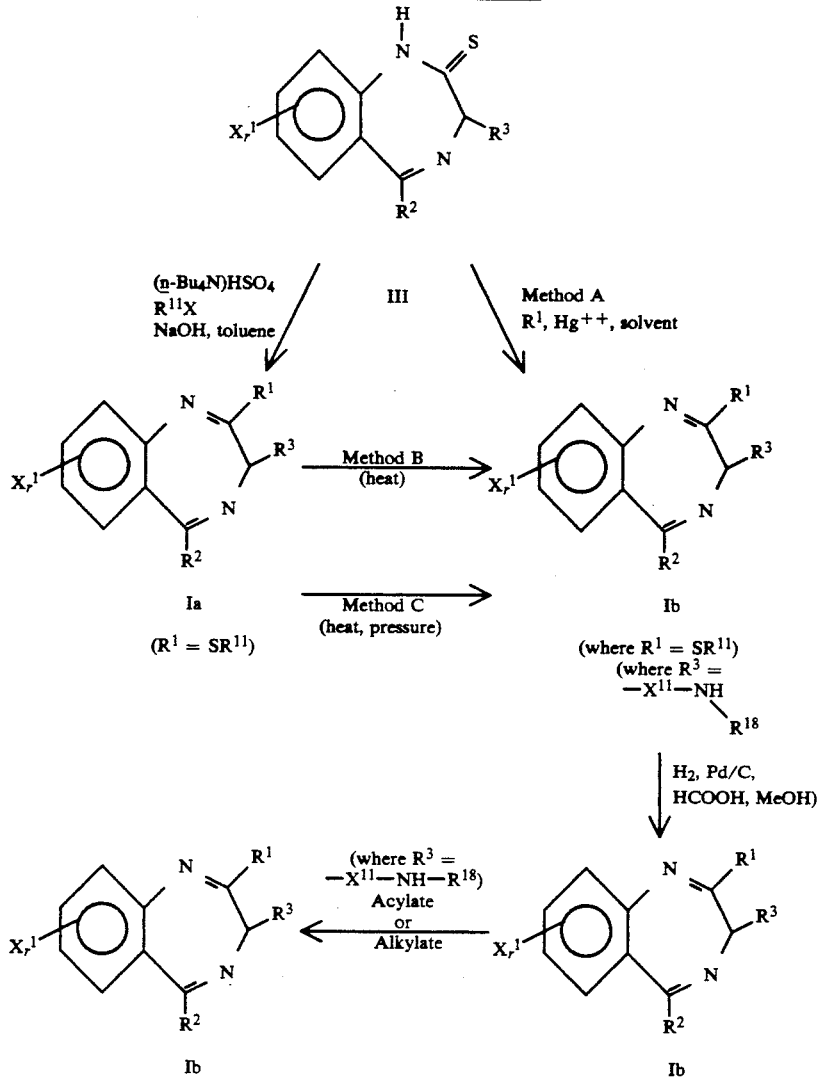

Referring to Scheme I, the compounds of Formula I are prepared as follows:

1,3-Dihydro-3,5-disubstituted-1,4-benzodiazepines IV are reacted with phosphorus pentasulfide or preferably Lawesson's reagent (2,4-bis-(4-methoxyphenyl)-2,4-dithioxo-1,3,2,4-dithiadiphosphetane) in an aprotic solvent, preferably toluene at room temperature to the boiling point of the solvent, to give the corresponding thioamides III.

Treatment of the benzodiazepin-2-thiones III with an alcohol or an amine in a solvent, preferably tetrahydrofuran, in the presence of a mercury salt such as mercuric chloride or mercuric acetate affords the title compound Ib, (Method A).

Alternatively, the benzodiazepin-2-thiones III can be converted to the title compound thioiminoethers Ia with an alkylating agent, preferably a lower alkyl halide or cycloloweralkyl halide, at room temperature, under phase transfer conditions requiring aqueous base, such as an alkali earth hydroxide, an organic solvent immiscible with water, preferably toluene and a catalyst, preferably, tetra-n-butylammonium hydrogen sulfate. The thioiminoethers Ia are, in turn, transformed to the title compounds Ib by reaction with an amine or alcohol for 2-96 hours preferably 24 hours, at room temperature to the boiling point of the reagent, preferably 80° C., (Method B). Compounds of formula Ib are also accessible by heating iminoethers Ia with an amine or alcohol in a sealed pressure vessel at 80°-250° C., preferably 120° C., for 1-36 hours, preferably 12 hours, (Method C).

When $R^3$ in compounds of Formula IV contains an amino, keto, or alcohol moiety, this moiety should be protected during the synthesis of Ia or Ib according to methods known in the art. Removal of such protecting groups according to methods known in the art at the end the synthesis provides Ia or Ib.

For the case of $R^3$ containing a funtionalized amino group, Scheme I is performed on IV,

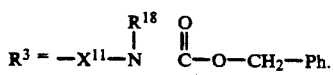

The protecting group is then removed from Ib by catalytic transfer hydrogenolysis, and the resultant amine

[Ib, $R^3 = -X^{12}-NH-R^{18}$] is derivatized appropriately, e.g. with an acid $HOOC-(CH_2)_q-R^7$ to give Ib,

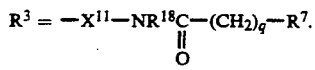

In cases where the starting materials are optically active, the chirality at $C_3$ is controlled by the synthesis. When racemic starting materials are employed, racemic mixtures are obtained. The enantiomers may be separated by resolution.

In Vitro Activity of Formula I

The biological activity of the compounds of Formula I have been evaluated using 1) an $^{125}$I-CCK receptor binding assay and in vitro isolated tissue preparations and 2) $^{125}$I-gastrin and $^3$H-pentagastrin binding assays.

Materials and Methods

1. CCK Receptor Binding (Pancreas)

CCK-33 was radiolabeled with $^{125}$I-Bolton Hunter reagent (2000 Ci/mmole) as described by Sankara et al. (*J. Biol. Chem.* 254: 9349-9351, 1979). Receptor binding was performed according to Innis and Snyder (*Proc. Natl. Acad. Sci.* 77: 6917-6921, 1980) with the minor modification of adding the additional protease inhibitors, phenyl-methane sulfonyl fluoride and o-phenanthroline. The latter two compounds have no effect on the $^{125}$I-CCK receptor binding assay.

Male Sprague-Dawley rats (200–350g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothrietol, 0.1 mM bacitracin, 1.2 mM phenylmethane sulfonyl fluoride and 0.5 mM o-phenanthroline). For the binding assay, 25 μl of buffer (for total binding) or unlabeled CCK-8 sulfate to give a final concentration of 1 μM (for nonspecific binding) or the compounds of Formula I (for determination of inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (*Ann. N.Y. Acad. Sci.* 51: 660, 1949), $^{125}$I-CCK-33 was progressively diluted with increasing concentrations of CCK-33.

2. CCK Receptor Binding (Brain)

CCK-33 was radiolabeled and the binding was performed according to the description for the pancreas method with modifications according to Saito et al., J. Neurochem. 37, 483–490, 1981.

Male Hartley guinea pigs (300–500 g) were sacrificed by decapitation and the brains were removed and placed in ice-cold 50 mM, Tris HCl plus 7.58 g/l Trizma-7.4 (pH 7.4 at 25° C.). Cerebral cortex was dissected and used as a receptor source. Each gram of fresh guinea pig brain tissue was homogenized in 10 ml of Tris Trizma buffer with a Brinkman polytron PT-10. The homogenates were centrifuged at 42,000 g for 15 min. Pellets were resuspended in Tris Buffer, centrifuged as above and resuspended in 200 volumes of binding assay buffer (10 mM N-2-hydroxyethyl-piperazine-N'-2-ethane sulfonic acid (HEPES), 5 mM MgCl$_2$, 0.25 mg/ml bacitracin, 1 mM ethylene glycol-bis-(β-aminoethyl-ether-N,N'-tetraacetic acid (EGTA), and 0.4% bovine serum albumin (BSA)). For the binding assay, 25 μl of buffer (for total binding) or unlabeled CCK-8 sulfate to give a final concentration of 1 μM (for nonspecific binding) or the compounds of Formula I (for determination of inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

The compounds of Formula I can be determined to be competitive antagonists of CCK according to the following assays.

3. Isolated guinea pig gall bladder

Male Hartley guinea pigs (400–600 g) are sacrificed by decapitation. The whole gall bladder is dissected free from adjacent tissues and cut into two equal halves. The gall bladder strips are suspended along the axis of the bile duct in a 5 ml organ bath under 1 g tension. The organ bath contains a Kreb's bicarbonate solution (NaCl 118 mM, KCl 4.75 mM, CaCl 2.54 mM, KH$_2$PO$_4$ 1.19 mM, Mg SO$_4$ 1.2 mM, NaHCO$_3$ 25 mM and dextrose 11 mM) maintained at 32° C. and bubbled with 95% O$_2$ and 5% CO$_2$. Isometric contractions are recorded using Statham (60 g; 0.12 mm) strain gauges and a Hewlett-Packard (77588) recorder. The tissues are washed every 10 minutes for 1 hr to obtain equilibrium prior to the beginning of the study. CCK-8 is added cumulatively to the baths and EC$_{50}$'s determined using regression analysis. After washout (every 10 minutes for 1 hr), the compound of Formula I is added at least 5 minutes before the addition of CCK-8 and the EC$_{50}$ of CCK-8 in the presence of the compound of Formula I similarly determined.

4. Isolated longitudinal muscle of guinea pig ileum

Longitudinal muscle strips with attached nerve plexus are prepared as described in *Brit J. Pharmac.* 23: ; 356–363, 1964; *J. Physiol.* 194: 13–33, 1969. Male Hartley guinea pigs are decapitated and the ileum removed (10 cm of the terminal ileum is discarded and the adjacent 20 cm piece used). A piece (10 cm) of the ileum is stretched on a glass pipette. Using a cotton applicator to stroke tangentially away from the mesentery attachment at one end, the longitudinal muscle is separated from the underlying circular muscle. The longitudinal muscle is then tied to a thread and by gently pulling, stripped away from the entire muscle. A piece of approximately 2 cm is suspended in 5 ml organ bath containing Krebs solution and bubbled with 95% O$_2$ and 5% CO$_2$ at 37° C. under 0.5 g tension. CCK-8 is added cumulatively to the baths and EC$_{50}$ values in the presence and absence of compounds of Formula I determined as described in the gall bladder protocol (above).

5. Gastrin Antagonism

Gastrin antagonist activity of compounds of Formula I is determined using the following assay:

Gastrin Receptor Binding in Guinea Pig Gastric Glands
Preparation of guinea pig gastric mucosal glands Guinea pig gastric mucosal glands were prepared by the procedure of Berglingh and Obrink Acta Physiol. Scand. 96: 150 (1976) with a slight modification according to Praissman et al. C. J. Receptor Res. 3: (1983). Gastric mucosa from guinea pigs (300–500 g body weight, male Hartley) were washed thoroughly and minced with fine scissors in standard buffer consisting of the following: 130 mM NaCl, 12 mM NaHCO$_3$, 3 mM NaH$_2$PO$_4$, 3 mM K$_2$HPO$_4$, 2 mM MgSO$_4$, 1 mM CaCl$_2$, 5 mM glucose and 4 mM L-glutamine, 25 mM HEPES at pH 7.4. The minced tissues were washed and then incubated in a 37° C. shaker bath for 40 minutes with the buffer containing 0.1% collagenase and 0.1% BSA and bubbled with 95% O$_2$ and 5% CO$_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

In Vitro Results

1. Effect of The Compounds of Formula I on $^{125}$I-CCK-33 receptor binding

The preferred compounds of Formula I are those which inhibited specific $^{125}$I-CCK-33 binding in a concentration dependent manner.

Scatchard analysis of specific $^{125}$I-CCK-33 receptor binding in the absence and presence of the compounds of Formula I indicated the compound of Formula I competitively inhibited specific $^{125}$I-CCK-33 receptor binding since it increased the K$_D$ (dissociation constant) without affecting the B$_{max}$ (maximum receptor number). A K$_i$ value (dissociation constant of inhibitor) of the compounds of Formula I was estimated.

The data of Table 1 were obtained for compounds of the following structure:

TABLE 1
RECEPTOR BINDING RESULTS

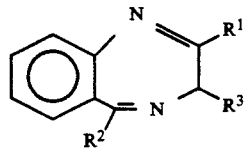

| | | | | IC$^{50}$ (mM) | | |
| --- | --- | --- | --- | --- | --- | --- |
| Example | R$^1$ | R$^2$ | R$^3$ | $^{125}$I-CCK Pancreas | $^{125}$I-CCK Brain | Gastrin |
| 1 | PhNH | o-F-Ph | 3-indolyl-methyl | 34 | 100 | — |
| 2 | CH$_3$S | o-F-Ph | 3-indolyl-methyl | 17 | — | — |
| 3 | NH$_2$ | o-F-Ph | 3-indolyl-methyl | 1.7 | — | — |
| 4 | CH$_3$NH | o-F-Ph | 3-indolyl-methyl | 4.5 | >100 | 67 |
| 5 | CH$_3$CH$_2$O$_2$CNH | o-F-Ph | 3-indolyl-methyl | 23 | 49 | — |
| 6 | NC—NH | o-F-Ph | 3-indolyl-methyl | 2.0 | 100 | — |
| 7 | CH$_3$CH$_2$CH$_2$NH | o-F-Ph | 3-indolyl-methyl | 2.7 | >100 | — |
| 8 | HO$_2$C—CH$_2$NH | o-F-Ph | 3-indolyl-methyl | 3.6 | 31 | 2.7 |
| 9 | HO$_2$C—CH$_2$NH | Ph | NHCNH—C$_6$H$_4$—Cl (with C=O) | 0.069 | 0.11 | 0.032 |
| 10 | CH$_3$CH$_2$O$_2$C—CH$_2$NH | Ph | NHCNH—C$_6$H$_4$—Cl (with C=O) | 1.4 | 0.27 | 0.26 |
| 11 | piperidinyl-C(O)-CH$_2$—NH | Ph | | 1.1 | 0.0059 | 0.02 |
| 12 | CH$_3$—N(piperazinyl)N—CH$_2$—NH | Ph | | 1.0 | 0.124 | 0.180 |

TABLE 1-continued
RECEPTOR BINDING RESULTS

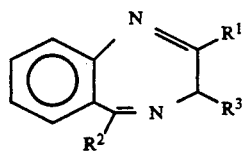

| Example | R¹ | R² | R³ | IC⁵⁰ (mM) | | |
|---|---|---|---|---|---|---|
| | | | | $^{125}$I-CCK Pancreas | $^{125}$I-CCK Brain | Gastrin |
| 13 | Et$_2$N—(CH$_2$)$_3$—NH | Ph | | 14 | 0.078 | 0.120 |
| 14 | 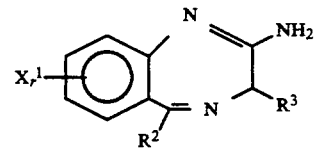 | Ph | | 0.59 | 0.015 | 0.013 |

Preferred compounds of Formula I are those where R¹ is —NH$_2$, —NH(CH$_2$)$_{0-2}$—CH$_3$,

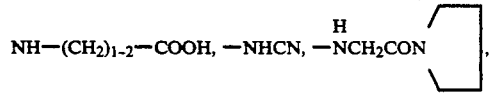

NH—(CH$_2$)$_{1-2}$—COOH, —NHCN, —NCH$_2$CON

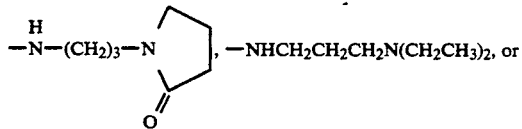

—N—(CH$_2$)$_3$—N , —NHCH$_2$CH$_2$CH$_2$N(CH$_2$CH$_3$)$_2$, or

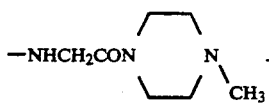

—NHCH$_2$CON  N—CH$_3$ .

Other series of preferred compounds are those wherein R² is phenyl, p-chlorophenyl, o-chlorophenyl, o-fluorophenyl, 2,4-dichlorophenyl, 2,6-difluorophenyl, —CH$_2$COO-t-butyl, or —CH$_2$COOEt.

Other series of preferred compounds are those where R³ is 2- or 3-indolylmethyl; NHCO-R⁷ where R⁷ is 2-indolyl, 2-(1-methylindolyl), 2-(5-fluoroindolyl), 2-benzofuranyl, 2-benzothienyl, 2-(3-methylindenyl), phenylethenyl, mono- or dihalophenyl, mono- or dimethyl or trifluoromethylphenyl; NHCONH-p-chlorophenyl, NHCONH-m-methylphenyl, NHCONH-p-methylphenyl, or NHCONH-m-methoxyphenyl.

It is preferred that X¹$_r$ is H, Cl, F, CF$_3$, OH or NO$_2$.

Examples of Formula I compounds are tabulated below.

TABLE 2
Compounds of the formula:

| X¹ | r | R² | R³ |
|---|---|---|---|
| H | 1 | o-F-Ph | —CH$_2$-2-indolyl |
| H | 1 | o-F-Ph | —CH$_2$-3-indolyl |
| H | 1 | o-F-Ph | NH(CH$_2$)$_{1-3}$-3-indolyl |
| H | 1 | o-F-Ph | —NHCH$_2$—(CH$_2$)$_2$-3-indolyl<br>         \|<br>      COOEt |
| H | 1 | o-F-Ph | —CH$_2$NH(CH$_2$)$_2$-3-indolyl |
| H | 1 | o-F-Ph | —NHCO-(CH$_2$)$_{0-2}$-2-indolyl |
| H | 1 | o-F-Ph | —NHCO(CH$_2$)$_{0-2}$-3-indolyl |
| H | 1 | o-F-Ph | NHCO-p-halo-phenyl |
| H | 1 | o-F-Ph | NHCO-m-halo-phenyl |
| H | 1 | o-F-Ph | NHCO-2-benzofuranyl |
| H | 1 | o-F-Ph | 2-(3-methylindenyl) |
| H | 1 | o-F-Ph | phenylethenyl |
| H | 1 | o-F-Ph | NHCONH-p-halophenyl |
| H | 1 | p-Cl-Ph | —CH$_2$-2-indolyl |
| H | 1 | p-Cl-Ph | —CH$_2$-3-indolyl |
| H | 1 | p-Cl-Ph | —NH(CH$_2$)$_{1-3}$-3-indolyl |
| H | 1 | p-Cl-Ph | —NHCO-(CH$_2$)$_{0-2}$-2-indolyl |
| H | 1 | p-Cl-Ph | NHCO-p-halo-phenyl |
| H | 1 | p-Cl-Ph | NHCO-m-halo-phenyl |
| H | 1 | p-Cl-Ph | NHCO-2-benzofuranyl |
| H | 1 | p-Cl-Ph | 2-(3-methylindenyl) |
| H | 1 | p-Cl-Ph | phenylethenyl |
| H | 1 | p-Cl-Ph | NHCONH-p-halo-phenyl |
| H | 1 | phenyl | —CH$_2$-2-indolyl |
| H | 1 | phenyl | —CH$_2$-3-indolyl |
| H | 1 | phenyl | —NHCO(CH$_2$)$_{0-2}$-indolyl |
| H | 1 | phenyl | —NH(CH$_2$)$_{1-3}$-3-indolyl |
| H | 1 | phenyl | NHCO-p-halo-phenyl |
| H | 1 | phenyl | NHCO-m-halo-phenyl |
| H | 1 | phenyl | NHCO-2-benzofuranyl |
| H | 1 | phenyl | 2-(3-methylindenyl) |
| H | 1 | phenyl | phenylethenyl |
| H | 1 | phenyl | NHCONH-p-halo-phenyl |
| H | 1 | p-F-Ph | —CH$_2$-2-indolyl |
| H | 1 | p-F-Ph | —CH$_2$-3-indolyl |
| H | 1 | p-F-Ph | —NHCO(CH$_2$)$_{0-2}$-2-indolyl |
| H | 1 | p-F-Ph | —NH(CH$_2$)$_{1-3}$-3-indolyl |
| H | 1 | p-F-Ph | NHCO-p-halo-phenyl |
| H | 1 | p-F-Ph | NHCO-m-halo-phenyl |

TABLE 2-continued

Compounds of the formula:

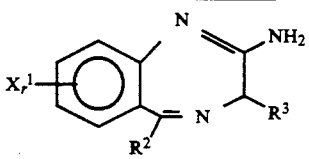

| X¹ | r | R² | R³ |
|---|---|---|---|
| H | 1 | p-F-Ph | NHCO-2-benzofuranyl |
| H | 1 | p-F-Ph | 2-(3-methylindenyl) |
| H | 1 | p-F-Ph | phenylethenyl |
| H | 1 | p-F-Ph | NHCONH-p-halophenyl |
| H | 1 | 2,4-di-Cl-Ph | —CH$_2$-2-indolyl |
| H | 1 | 2,4-di-Cl-Ph | —CH$_2$-3-indolyl |
| H | 1 | 2,4-di-Cl-Ph | —NHCO(CH$_2$)$_{0\text{-}2}$-2-indolyl |
| H | 1 | 2,4-di-Cl-Ph | —NH(CH$_2$)$_{1\text{-}3}$-3-indolyl |
| H | 1 | 2,4-di-Cl-Ph | NHCO-p-halo-phenyl |
| H | 1 | 2,4-di-Cl-Ph | NHCO-m-halo-phenyl |
| H | 1 | 2,4-di-Cl-Ph | NHCO-2-benzofuranyl |
| H | 1 | 2,4-di-Cl-Ph | 2-(3-methylindenyl) |
| H | 1 | 2,4-di-Cl-Ph | phenylethenyl |
| H | 1 | 2,4-di-Cl-Ph | NHCONH-p-halophenyl |
| H | 1 | 2,6-di-F-Ph | —CH$_2$-2-indolyl |
| H | 1 | 2,6-di-F-Ph | —CH$_2$-3-indolyl |
| H | 1 | 2,6-di-F-Ph | —NHCO(CH$_2$)$_{0\text{-}2}$-2-indolyl |
| H | 1 | 2,6-di-F-Ph | —NH(CH$_2$)$_{1\text{-}3}$-3-indolyl |
| H | 1 | 2,6-di-F-Ph | NHCO-p-halo-phenyl |
| H | 1 | 2,6-di-F-Ph | NHCO-m-halo-phenyl |
| H | 1 | 2,6-di-F-Ph | NHCO-2-benzofuranyl |
| H | 1 | 2,6-di-F-Ph | 2-(3-methylindenyl) |
| H | 1 | 2,6-di-F-Ph | phenylethenyl |
| H | 1 | 2,6-di-F-Ph | NHCONH-p-halo-phenyl |
| H | 1 | CH$_2$COO-t-butyl | —CH$_2$-2-indolyl |
| H | 1 | CH$_2$COO-t-butyl | —CH$_2$-3-indolyl |
| H | 1 | CH$_2$COO-t-butyl | —NHCO(CH$_2$)$_{0\text{-}2}$-2-indolyl |
| H | 1 | CH$_2$COO-t-butyl | —NH(CH$_2$)$_{1\text{-}3}$-3-indolyl |
| H | 1 | CH$_2$COO-t-butyl | NHCO-p-halo-phenyl |
| H | 1 | CH$_2$COO-t-butyl | NHCO-m-halo-phenyl |
| H | 1 | CH$_2$COO-t-butyl | NHCO-2-benzofuranyl |
| H | 1 | CH$_2$COO-t-butyl | 2-(3-methylindenyl) |
| H | 1 | CH$_2$COO-t-butyl | phenylethenyl |
| H | 1 | CH$_2$COO-t-butyl | NHCONH-p-halophenyl |
| H | 1 | —CH$_2$COOEt | —CH$_2$-2-indolyl |
| H | 1 | —CH$_2$COOEt | —CH$_2$-3-indolyl |
| H | 1 | —CH$_2$COOEt | —NHCO(CH$_2$)$_{0\text{-}2}$-2-indolyl |
| H | 1 | —CH$_2$COOEt | —NH(CH$_2$)$_{1\text{-}3}$-3-indolyl |
| H | 1 | —CH$_2$COOEt | NHCO-p-halo-phenyl |
| H | 1 | —CH$_2$COOEt | NHCO-m-halo-phenyl |
| H | 1 | —CH$_2$COOEt | NHCO-2-benzofuranyl |
| H | 1 | —CH$_2$COOEt | 2-(3-methylindenyl) |
| H | 1 | —CH$_2$COOEt | phenylethenyl |
| H | 1 | —CH$_2$COOEt | NHCONH-p-halophenyl |
| Cl | 1 | p-Cl-Ph | —CH$_2$-2-indolyl |
| Cl | 1 | p-Cl-Ph | —CH$_2$-3-indolyl |
| Cl | 1 | p-Cl-Ph | —NHCO(CH$_2$)$_{0\text{-}2}$-2-indolyl |
| Cl | 1 | p-Cl-Ph | —NH(CH$_2$)$_{1\text{-}3}$-3-indolyl |
| Cl | 1 | p-Cl-Ph | NHCO-p-halo-phenyl |
| Cl | 1 | p-Cl-Ph | NHCO-m-halo-phenyl |
| Cl | 1 | p-Cl-Ph | NHCO-2-benzofuranyl |
| Cl | 1 | p-Cl-Ph | 2-(3-methylindenyl) |
| Cl | 1 | p-Cl-Ph | phenylethenyl |
| Cl | 1 | p-Cl-Ph | NHCONH-p-halophenyl |
| Cl | 1 | Ph | —CH$_2$-2-indolyl |
| Cl | 1 | Ph | —CH$_2$-3-indolyl |
| Cl | 1 | Ph | —NHCO(CH$_2$)$_{0\text{-}2}$-2-indolyl |
| Cl | 1 | Ph | —NH(CH$_2$)$_{1\text{-}3}$-3-indolyl |
| Cl | 1 | Ph | NHCO-p-halo-phenyl |
| Cl | 1 | Ph | NHCO-m-halo-phenyl |
| Cl | 1 | Ph | NHCO-2-benzofuranyl |
| Cl | 1 | Ph | 2-(3-methylindenyl) |
| Cl | 1 | Ph | phenylethenyl |
| Cl | 1 | Ph | NHCONH-p-halophenyl |
| Cl | 1 | o-F-Ph | —CH$_2$-2-indolyl |
| Cl | 1 | o-F-Ph | —CH$_2$-3-indolyl |
| Cl | 1 | o-F-Ph | —NHCO(CH$_2$)$_{0\text{-}2}$-2-indolyl |
| Cl | 1 | o-F-Ph | —NH(CH$_2$)$_{1\text{-}3}$-3-indolyl |
| Cl | 1 | o-F-Ph | NHCO-p-halo-phenyl |
| Cl | 1 | o-F-Ph | NHCO-m-halo-phenyl |
| Cl | 1 | o-F-Ph | NHCO-2-benzofuranyl |

TABLE 2-continued

Compounds of the formula:

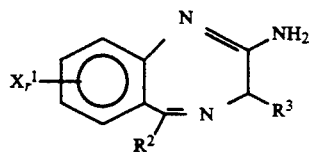

| X¹ | r | R² | R³ |
|---|---|---|---|
| Cl | 1 | o-F-Ph | 2-(3-methylindenyl) |
| Cl | 1 | o-F-Ph | phenylethenyl |
| Cl | 1 | o-F-Ph | NHCONH-p-halophenyl |
| Cl | 1 | p-F-Ph | —CH$_2$-2-indolyl |
| Cl | 1 | p-F-Ph | —CH$_2$-3-indolyl |
| Cl | 1 | p-F-Ph | —NHCO(CH$_2$)$_{0\text{-}2}$-2-indolyl |
| Cl | 1 | p-F-Ph | —NH(CH$_2$)$_{1\text{-}3}$-3-indolyl |
| Cl | 1 | p-F-Ph | NHCO-p-halo-phenyl |
| Cl | 1 | p-F-Ph | NHCO-m-halo-phenyl |
| Cl | 1 | p-F-Ph | NHCO-2-benzofuranyl |
| Cl | 1 | p-F-Ph | 2-(3-methylindenyl) |
| Cl | 1 | p-F-Ph | phenylethenyl |
| Cl | 1 | p-F-Ph | NHCONH-p-halophenyl |
| F | 1 | 2,4-di-Cl-Ph | —CH$_2$-2-indolyl |
| F | 1 | 2,4-di-Cl-Ph | —CH$_2$-3-indolyl |
| F | 1 | 2,4-di-Cl-Ph | —NHCO(CH$_2$)$_{0\text{-}2}$-2-indolyl |
| F | 1 | 2,4-di-Cl-Ph | —NH(CH$_2$)$_{1\text{-}3}$-3-indolyl |
| F | 1 | 2,4-di-Cl-Ph | NHCO-p-halo-phenyl |
| F | 1 | 2,4-di-Cl-Ph | NHCO-m-halo-phenyl |
| F | 1 | 2,4-di-Cl-Ph | NHCO-2-benzofuranyl |
| F | 1 | 2,4-di-Cl-Ph | 2-(3-methylindenyl) |
| F | 1 | 2,4-di-Cl-Ph | phenylethenyl |
| F | 1 | 2,4-di-Cl-Ph | NHCONH-p-halophenyl |
| F | 1 | 2,6-di-F-Ph | —CH$_2$-2-indolyl |
| F | 1 | 2,6-di-F-Ph | —CH$_2$-3-indolyl |
| F | 1 | 2,6-di-F-Ph | —NHCO(CH$_2$)$_{0\text{-}2}$-2-indolyl |
| F | 1 | 2,6-di-F-Ph | —NH(CH$_2$)$_{1\text{-}3}$-3-indolyl |
| F | 1 | 2,6-di-F-Ph | NHCO-p-halo-phenyl |
| F | 1 | 2,6-di-F-Ph | NHCO-m-halo-phenyl |
| F | 1 | 2,6-di-F-Ph | NHCO-2-benzofuranyl |
| F | 1 | 2,6-di-F-Ph | 2-(3-methylindenyl) |
| F | 1 | 2,6-di-F-Ph | phenylethenyl |
| F | 1 | 2,6-di-F-Ph | NHCONH-p-halophenyl |
| F | 1 | COO-t-butyl | —CH$_2$-2-indolyl |
| F | 1 | COO-t-butyl | —CH$_2$-3-indolyl |
| F | 1 | COO-t-butyl | —NHCO(CH$_2$)$_{0\text{-}2}$-2-indolyl |
| F | 1 | COO-t-butyl | —NH(CH$_2$)$_{1\text{-}3}$-3-indolyl |
| F | 1 | COO-t-butyl | NHCO-p-halo-phenyl |
| F | 1 | COO-t-butyl | NHCO-m-halo-phenyl |
| F | 1 | COO-t-butyl | NHCO-2-benzofuranyl |
| F | 1 | COO-t-butyl | 2-(3-methylindenyl) |
| F | 1 | COO-t-butyl | phenylethenyl |
| F | 1 | COO-t-butyl | NHCONH-p-halophenyl |
| F | 1 | —CH$_2$COOEt | —CH$_2$-2-indolyl |
| F | 1 | —CH$_2$COOEt | —CH$_2$-3-indolyl |
| F | 1 | —CH$_2$COOEt | —NHCO(CH$_2$)$_{0\text{-}2}$-2-indolyl |
| F | 1 | —CH$_2$COOEt | —NH(CH$_2$)$_{1\text{-}3}$-3-indolyl |
| F | 1 | —CH$_2$COOEt | NHCO-p-halo-phenyl |
| F | 1 | —CH$_2$COOEt | NHCO-m-halo-phenyl |
| F | 1 | —CH$_2$COOEt | NHCO-2-benzofuranyl |
| F | 1 | —CH$_2$COOEt | 2-(3-methylindenyl) |
| F | 1 | —CH$_2$COOEt | phenylethenyl |
| F | 1 | —CH$_2$COOEt | NHCONH-p-halophenyl |
| CF$_3$ | 1 | p-Cl-Ph | —CH$_2$-2-indolyl |
| CF$_3$ | 1 | p-Cl-Ph | —CH$_2$-3-indolyl |
| CF$_3$ | 1 | p-Cl-Ph | —NHCO(CH$_2$)$_{0\text{-}2}$-2-indolyl |
| CF$_3$ | 1 | p-Cl-Ph | —NH(CH$_2$)$_{1\text{-}3}$-3-indolyl |
| CF$_3$ | 1 | p-Cl-Ph | NHCO-p-halo-phenyl |
| CF$_3$ | 1 | p-Cl-Ph | NHCO-m-halo-phenyl |
| CF$_3$ | 1 | p-Cl-Ph | NHCO-2-benzofuranyl |
| CF$_3$ | 1 | p-Cl-Ph | 2-(3-methylindenyl) |
| CF$_3$ | 1 | p-Cl-Ph | phenylethenyl |
| CF$_3$ | 1 | p-Cl-Ph | NHCONH-p-halo-phenyl |
| CF$_3$ | 1 | Ph | —CH$_2$-2-indolyl |
| CF$_3$ | 1 | Ph | —CH$_2$-3-indolyl |
| CF$_3$ | 1 | Ph | —NHCO(CH$_2$)$_{0\text{-}2}$-2-indolyl |
| CF$_3$ | 1 | Ph | —NH(CH$_2$)$_{1\text{-}3}$-3-indolyl |
| CF$_3$ | 1 | Ph | NHCO-p-halo-phenyl |
| CF$_3$ | 1 | Ph | NHCO-m-halo-phenyl |
| CF$_3$ | 1 | Ph | NHCO-2-benzofuranyl |
| CF$_3$ | 1 | Ph | 2-(3-methylindenyl) |

TABLE 2-continued

Compounds of the formula:

$$X_r^1 \text{—[benzene ring with } N\text{=}C(NH_2)\text{—N(R}^3)\text{—C(R}^2)\text{=] fused diazine}$$

| $X^1$ | r | $R^2$ | $R^3$ |
|---|---|---|---|
| CF$_3$ | 1 | Ph | phenylethenyl |
| CF$_3$ | 1 | Ph | NHCONH-p-halo-phenyl |
| CF$_3$ | 1 | o-F-Ph | —CH$_2$-2-indolyl |
| CF$_3$ | 1 | o-F-Ph | —CH$_2$-3-indolyl |
| CF$_3$ | 1 | o-F-Ph | —NHCO(CH$_2$)$_{0-2}$-2-indolyl |
| CF$_3$ | 1 | o-F-Ph | —NH(CH$_2$)$_{1-3}$-3-indolyl |
| CF$_3$ | 1 | o-F-Ph | NHCO-p-halo-phenyl |
| CF$_3$ | 1 | o-F-Ph | NHCO-m-halo-phenyl |
| CF$_3$ | 1 | o-F-Ph | NHCO-2-benzofuranyl |
| CF$_3$ | 1 | o-F-Ph | 2-(3-methylindenyl) |
| CF$_3$ | 1 | o-F-Ph | phenylethenyl |
| CF$_3$ | 1 | o-F-Ph | NHCONH-p-halo-phenyl |
| CF$_3$ | 1 | p-F-Ph | —CH$_2$-2-indolyl |
| CF$_3$ | 1 | p-F-Ph | —CH$_2$-3-indolyl |
| CF$_3$ | 1 | p-F-Ph | —NHCO(CH$_2$)$_{0-2}$-2-indolyl |
| CF$_3$ | 1 | p-F-Ph | —NH(CH$_2$)$_{1-3}$-3-indolyl |
| CF$_3$ | 1 | p-F-Ph | NHCO-p-halo-phenyl |
| CF$_3$ | 1 | p-F-Ph | NHCO-m-halo-phenyl |
| CF$_3$ | 1 | p-F-Ph | NHCO-2-benzofuranyl |
| CF$_3$ | 1 | p-F-Ph | 2-(3-methylindenyl) |
| CF$_3$ | 1 | p-F-Ph | phenylethenyl |
| CF$_3$ | 1 | p-F-Ph | NHCONH-p-halo-phenyl |
| NO$_2$ | 1 | p-Cl-Ph | —CH$_2$-2-indolyl |
| NO$_2$ | 1 | p-Cl-Ph | —CH$_2$-3-indolyl |
| NO$_2$ | 1 | p-Cl-Ph | —NHCO(CH$_2$)$_{0-2}$-2-indolyl |
| NO$_2$ | 1 | p-Cl-Ph | —NH(CH$_2$)$_{1-3}$-3-indolyl |
| NO$_2$ | 1 | p-Cl-Ph | NHCO-p-halo-phenyl |
| NO$_2$ | 1 | p-Cl-Ph | NHCO-m-halo-phenyl |
| NO$_2$ | 1 | p-Cl-Ph | NHCO-2-benzofuranyl |
| NO$_2$ | 1 | p-Cl-Ph | 2-(3-methylindenyl) |
| NO$_2$ | 1 | p-Cl-Ph | phenylethenyl |
| NO$_2$ | 1 | p-Cl-Ph | NHCONH-p-halo-phenyl |
| NO$_2$ | 1 | Ph | —CH$_2$-2-indolyl |
| NO$_2$ | 1 | Ph | —CH$_2$-3-indolyl |
| NO$_2$ | 1 | Ph | —NHCO(CH$_2$)$_{0-2}$-2-indolyl |
| NO$_2$ | 1 | Ph | —NH(CH$_2$)$_{1-3}$-3-indolyl |
| NO$_2$ | 1 | Ph | NHCO-p-halo-phenyl |
| NO$_2$ | 1 | Ph | NHCO-m-halo-phenyl |
| NO$_2$ | 1 | Ph | NHCO-2-benzofuranyl |
| NO$_2$ | 1 | Ph | 2-(3-methylindenyl) |
| NO$_2$ | 1 | Ph | phenylethenyl |
| NO$_2$ | 1 | Ph | NHCONH-p-halo-phenyl |
| NO$_2$ | 1 | o-F-Ph | —CH$_2$-2-indolyl |
| NO$_2$ | 1 | o-F-Ph | —CH$_2$-3-indolyl |
| NO$_2$ | 1 | o-F-Ph | —NHCO(CH$_2$)$_{0-2}$-2-indolyl |
| NO$_2$ | 1 | o-F-Ph | —NH(CH$_2$)$_{1-3}$-3-indolyl |
| NO$_2$ | 1 | o-F-Ph | NHCO-p-halo-phenyl |
| NO$_2$ | 1 | o-F-Ph | NHCO-m-halo-phenyl |
| NO$_2$ | 1 | o-F-Ph | NHCO-2-benzofuranyl |
| NO$_2$ | 1 | o-F-Ph | 2-(3-methylindenyl) |
| NO$_2$ | 1 | o-F-Ph | phenylethenyl |
| NO$_2$ | 1 | o-F-Ph | NHCONH-p-halo-phenyl |
| NO$_2$ | 1 | p-F-Ph | —CH$_2$-2-indolyl |
| NO$_2$ | 1 | p-F-Ph | —CH$_2$-3-indolyl |
| NO$_2$ | 1 | p-F-Ph | —NHCO(CH$_2$)$_{0-2}$-2-indolyl |
| NO$_2$ | 1 | p-F-Ph | —NH(CH$_2$)$_{1-3}$-3-indolyl |
| NO$_2$ | 1 | p-F-Ph | NHCO-p-halo-phenyl |
| NO$_2$ | 1 | p-F-Ph | NHCO-m-halo-phenyl |
| NO$_2$ | 1 | p-F-Ph | NHCO-2-benzofuranyl |
| NO$_2$ | 1 | p-F-Ph | 2-(3-methylindenyl) |
| NO$_2$ | 1 | p-F-Ph | phenylethenyl |
| NO$_2$ | 1 | p-F-Ph | NHCONH-p-halo-phenyl |
| CH$_3$ | 1 | phenyl | —CH$_2$-2-indolyl |
| CH$_3$ | 1 | phenyl | —CH$_2$-3-indolyl |
| CH$_3$ | 1 | phenyl | —NHCO(CH$_2$)$_{0-2}$-2-indolyl |
| CH$_3$ | 1 | phenyl | —NH(CH$_2$)$_{1-3}$-3-indolyl |
| CH$_3$ | 1 | phenyl | NHCO-p-halo-phenyl |
| CH$_3$ | 1 | phenyl | NHCO-m-halo-phenyl |
| CH$_3$ | 1 | phenyl | NHCO-2-benzofuranyl |
| CH$_3$ | 1 | phenyl | 2-(3-methylindenyl) |
| CH$_3$ | 1 | phenyl | phenylethenyl |
| CH$_3$ | 1 | phenyl | NHCONH-p-halo-phenyl |
| H | 1 | o-F-Ph | —CH$_2$-2-indolyl |
| H | 1 | o-F-Ph | —CH$_2$-3-indolyl |
| H | 1 | o-F-Ph | —NHCO(CH$_2$)$_{0-2}$-2-indolyl |
| H | 1 | o-F-Ph | —NH(CH$_2$)$_{1-3}$-3-indolyl |
| H | 1 | o-F-Ph | NHCO-p-halo-phenyl |
| H | 1 | o-F-Ph | NHCO-m-halo-phenyl |
| H | 1 | o-F-Ph | NHCO-2-benzofuranyl |
| H | 1 | o-F-Ph | 2-(3-methylindenyl) |
| H | 1 | o-F-Ph | phenylethenyl |
| H | 1 | o-F-Ph | NHCONH-p-halo-phenyl |
| H | 1 | p-Cl-Ph | —CH$_2$-2-indolyl |
| H | 1 | p-Cl-Ph | —CH$_2$-3-indolyl |
| H | 1 | p-Cl-Ph | —NHCO(CH$_2$)$_{0-2}$-2-indolyl |
| H | 1 | p-Cl-Ph | —NH(CH$_2$)$_{1-3}$-3-indolyl |
| H | 1 | p-Cl-Ph | NHCO-p-halo-phenyl |
| H | 1 | p-Cl-Ph | NHCO-m-halo-phenyl |
| H | 1 | p-Cl-Ph | NHCO-2-benzofuranyl |
| H | 1 | p-Cl-Ph | 2-(3-methylindenyl) |
| H | 1 | p-Cl-Ph | phenylethenyl |
| H | 1 | p-Cl-Ph | NHCONH-p-halo-phenyl |
| H | 1 | o-F-Ph | CH$_2$-2 or 3-(1-methylindolyl) |
| H | 1 | —CH$_2$COO-t-butyl | CH$_2$-2 or 3-(1-methylindolyl) |
| H | 1 | —CH$_2$COOEt | CH$_2$-2 or 3-(1-methylindolyl) |
| H | 1 | Ph | CH$_2$-2 or 3-(1-methylindolyl) |
| H | 1 | —CH$_2$COO-t-butyl | NHCO(CH$_2$)$_{0-2}$-2-indolyl |
| H | 1 | —CH$_2$COOEt | NHCO(CH$_2$)$_{0-2}$-2-indolyl |
| H | 1 | Ph | NHCO(CH$_2$)$_{0-2}$-2-indolyl |
| H | 1 | o-F-Ph | NHCO(CH$_2$)$_{0-2}$-2 or 3-(1-methylindolyl) |
| H | 1 | —CH$_2$COO-t-butyl | NHCO(CH$_2$)$_{0-2}$-2 or 3-(1-methylindolyl) |
| H | 1 | —CH$_2$COOEt | NHCO(CH$_2$)$_{0-2}$-2 or 3-(1-methylindolyl) |
| H | 1 | Ph | NHCO(CH$_2$)$_{0-2}$-2 or 3-(1-methylindolyl) |
| H | 1 | o-F-Ph | NH(CH$_2$)$_{1-3}$-2-indolyl |
| H | 1 | —CH$_2$COO-t-butyl | NH(CH$_2$)$_{1-3}$-2-indolyl |
| H | 1 | —CH$_2$COOEt | NH(CH$_2$)$_{1-3}$-2-indolyl |
| H | 1 | Ph | NH(CH$_2$)$_{1-3}$-2-indolyl |
| H | 1 | o-F-Ph | NH(CH$_2$)$_{1-3}$-2 or 3-(1-methylindolyl) |
| H | 1 | —CH$_2$COO-t-butyl | NH(CH$_2$)$_{1-3}$-2 or 3-(1-methylindolyl) |
| H | 1 | —CH$_2$COOEt | NH(CH$_2$)$_{1-3}$-2 or 3-(1-methylindolyl) |
| H | 1 | Ph | NH(CH$_2$)$_{1-3}$-2 or 3-(1-methylindolyl) |
| H | 1 | o-F-Ph | NHCH(CH$_2$)$_2$-2-indolyl <br> \| <br> COOEt |
| H | 1 | —CH$_2$COO-t-butyl | NHCH(CH$_2$)$_2$-2-indolyl <br> \| <br> COOEt |
| H | 1 | —CH$_2$COOEt | NHCH(CH$_2$)$_2$-2-indolyl <br> \| <br> COOEt |
| H | 1 | Ph | NHCH(CH$_2$)$_2$-2-indolyl <br> \| <br> COOEt |
| H | 1 | o-F-Ph | COOEt <br> \| <br> NHCH(CH$_2$)$_2$-2 or 3-(1-methylindolyl) |

TABLE 2-continued

Compounds of the formula:

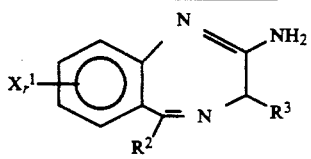

| X¹ | r | R² | R³ |
|---|---|---|---|
| H | 1 | —CH₂COO-t-butyl | COOEt<br>\|<br>NHCH(CH₂)₂-2<br>or 3-(1-methylindolyl) |
| H | 1 | —CH₂COOEt | COOEt<br>\|<br>NHCH(CH₂)₂-2<br>or 3-(1-methylindolyl) |
| H | 1 | Ph | COOEt<br>\|<br>NHCH(CH₂)₂-2 or 3-(1-methylindolyl) |
| H | 1 | o-F-Ph | NHCH(CH₂)₂-2 or 3-indolyl-<br>\|<br>COO-t-Butyl |
| H | 1 | —CH₂COO-t-butyl | NHCH(CH₂)₂-2 or 3-indolyl-<br>\|<br>COO-t-Butyl |
| H | 1 | —CH₂COOEt | NHCH(CH₂)₂-2 or 3-indolyl-<br>\|<br>COO-t-Butyl |

TABLE 2-continued

Compounds of the formula:

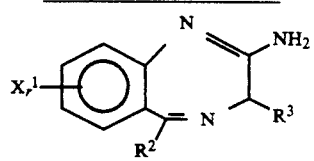

| X¹ | r | R² | R³ |
|---|---|---|---|
| H | 1 | Ph | NHCH(CH₂)₂-2 or 3-indolyl-<br>\|<br>COO-t-Butyl |
| H | 1 | o-F-Ph | COO-t-Butyl<br>\|<br>NHCH(CH₂)₂-2<br>or 3-(1-methylindolyl) |
| H | 1 | —CH₂COO-t-butyl | COO-t-Butyl<br>\|<br>NHCH(CH₂)₂-2<br>or 3-(1-methylindolyl) |
| H | 1 | —CH₂COOEt | COO-t-Butyl<br>\|<br>NHCH(CH₂)₂-2<br>or 3-(1-methylindolyl) |
| H | 1 | Ph | COO-t-Butyl<br>\|<br>NHCH(CH₂)₂-2<br>or 3-(1-methylindolyl) |

TABLE 3

Compounds of the formula:

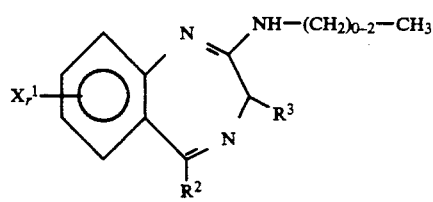

| X¹ | r | R² | R³ |
|---|---|---|---|
| H | 1 | o-F-Ph | —CH₂-2-indolyl |
| H | 1 | o-F-Ph | —CH₂-3-indolyl |
| H | 1 | o-F-Ph | NH(CH₂)₁₋₃-3-indolyl |
| H | 1 | o-F-Ph | —NHCH—(CH₂)₂-3-indolyl<br>\|<br>COOEt |
| H | 1 | o-F-Ph | —CH₂NH(CH₂)₂-3-indolyl |
| H | 1 | o-F-Ph | —NHCO—(CH₂)₀₋₂-2-indolyl |
| H | 1 | o-F-Ph | —NHCO(CH₂)₀₋₂-3-indolyl |
| H | 1 | o-F-Ph | NHCO-p-halo-phenyl |
| H | 1 | o-F-Ph | NHCO-m-halo-phenyl |
| H | 1 | o-F-Ph | NHCO-2-benzofuranyl |
| H | 1 | o-F-Ph | 2-(3-methylindenyl) |
| H | 1 | o-F-Ph | phenylethenyl |
| H | 1 | o-F-Ph | NHCONH-p-halo-phenyl |
| H | 1 | p-Cl-Ph | —CH₂-2-indolyl |
| H | 1 | p-Cl-Ph | —CH₂-3-indolyl |
| H | 1 | p-Cl-Ph | —NH(CH₂)₁₋₃-3-indolyl |
| H | 1 | p-Cl-Ph | —NHCO—(CH₂)₀₋₂-2-indolyl |
| H | 1 | p-Cl-Ph | NHCO-p-halo-phenyl |
| H | 1 | p-Cl-Ph | NHCO-m-halo-phenyl |
| H | 1 | p-Cl-Ph | NHCO-2-benzofuranyl |
| H | 1 | p-Cl-Ph | 2-(3-methylindenyl) |
| H | 1 | p-Cl-Ph | phenylethenyl |
| H | 1 | p-Cl-Ph | NHCONH-p-halo-phenyl |
| H | 1 | phenyl | —CH₂-2-indolyl |
| H | 1 | phenyl | —CH₂-3-indolyl |

TABLE 3-continued

Compounds of the formula:

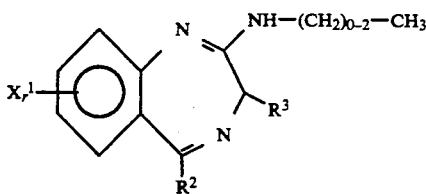

| X¹ | r | R² | R³ |
|---|---|---|---|
| H | 1 | phenyl | —NHCO(CH$_2$)$_{0-2}$-indolyl |
| H | 1 | phenyl | —NH(CH$_2$)$_{1-3}$-3-indolyl |
| H | 1 | phenyl | NHCO-p-halo-phenyl |
| H | 1 | phenyl | NHCO-m-halo-phenyl |
| H | 1 | phenyl | NHCO-2-benzofuranyl |
| H | 1 | phenyl | 2-(3-methylindenyl) |
| H | 1 | phenyl | phenylethenyl |
| H | 1 | phenyl | NHCONH-p-halo-phenyl |
| H | 1 | p-F-Ph | —CH$_2$-2-indolyl |
| H | 1 | p-F-Ph | —CH$_2$-3-indolyl |
| H | 1 | p-F-Ph | —NHCO(CH$_2$)$_{0-2}$-2-indolyl |
| H | 1 | p-F-Ph | —NH(CH$_2$)$_{1-3}$-3-indolyl |
| H | 1 | p-F-Ph | NHCO-p-halo-phenyl |
| H | 1 | p-F-Ph | NHCO-m-halo-phenyl |
| H | 1 | p-F-Ph | NHCO-2-benzofuranyl |
| H | 1 | p-F-Ph | 2-(3-methylindenyl) |
| H | 1 | p-F-Ph | phenylethenyl |
| H | 1 | p-F-Ph | NHCONH-p-halo-phenyl |
| H | 1 | 2,4-di-Cl-Ph | —CH$_2$-2-indolyl |
| H | 1 | 2,4-di-Cl-Ph | —CH$_2$-3-indolyl |
| H | 1 | 2,4-di-Cl-Ph | —NHCO(CH$_2$)$_{0-2}$-2-indolyl |
| H | 1 | 2,4-di-Cl-Ph | —NH(CH$_2$)$_{1-3}$-3-indolyl |
| H | 1 | 2,4-di-Cl-Ph | NHCO-p-halo-phenyl |
| H | 1 | 2,4-di-Cl-Ph | NHCO-m-halo-phenyl |
| H | 1 | 2,4-di-Cl-Ph | NHCO-2-benzofuranyl |
| H | 1 | 2,4-di-Cl-Ph | 2-(3-methylindenyl) |
| H | 1 | 2,4-di-Cl-Ph | phenylethenyl |
| H | 1 | 2,4-di-Cl-Ph | NHCONH-p-halo-phenyl |
| H | 1 | 2,6-di-F-Ph | —CH$_2$-2-indolyl |
| H | 1 | 2,6-di-F-Ph | —CH$_2$-3-indolyl |
| H | 1 | 2,6-di-F-Ph | —NHCO(CH$_2$)$_{0-2}$-2-indolyl |
| H | 1 | 2,6-di-F-Ph | —NH(CH$_2$)$_{1-3}$-3-indolyl |
| H | 1 | 2,6-di-F-Ph | NHCO-p-halo-phenyl |
| H | 1 | 2,6-di-F-Ph | NHCO-m-halo-phenyl |
| H | 1 | 2,6-di-F-Ph | NHCO-2-benzofuranyl |
| H | 1 | 2,6-di-F-Ph | 2-(3-methylindenyl) |
| H | 1 | 2,6-di-F-Ph | phenylethenyl |
| H | 1 | 2,6-di-F-Ph | NHCONH-p-halo-phenyl |
| H | 1 | CH$_2$COO-t-butyl | —CH$_2$-2-indolyl |
| H | 1 | CH$_2$COO-t-butyl | —CH$_2$-3-indolyl |
| H | 1 | CH$_2$COO-t-butyl | —NHCO(CH$_2$)$_{0-2}$-2-indolyl |
| H | 1 | CH$_2$COO-t-butyl | —NH(CH$_2$)$_{1-3}$-3-indolyl |
| H | 1 | CH$_2$COO-t-butyl | NHCO-p-halo-phenyl |
| H | 1 | CH$_2$COO-t-butyl | NHCO-m-halo-phenyl |
| H | 1 | CH$_2$COO-t-butyl | NHCO-2-benzofuranyl |
| H | 1 | CH$_2$COO-t-butyl | 2-(3-methylindenyl) |
| H | 1 | CH$_2$COO-t-butyl | phenylethenyl |
| H | 1 | CH$_2$COO-t-butyl | NHCONH-p-halo-phenyl |
| H | 1 | —CH$_2$COOEt | —CH$_2$-2-indolyl |
| H | 1 | —CH$_2$COOEt | —CH$_2$-3-indolyl |
| H | 1 | —CH$_2$COOEt | —NHCO(CH$_2$)$_{0-2}$-2-indolyl |
| H | 1 | —CH$_2$COOEt | —NH(CH$_2$)$_{1-3}$-3-indolyl |
| H | 1 | —CH$_2$COOEt | NHCO-p-halo-phenyl |
| H | 1 | —CH$_2$COOEt | NHCO-m-halo-phenyl |
| H | 1 | —CH$_2$COOEt | NHCO-2-benzofuranyl |
| H | 1 | —CH$_2$COOEt | 2-(3-methylindenyl) |
| H | 1 | —CH$_2$COOEt | phenylethenyl |
| H | 1 | —CH$_2$COOEt | NHCONH-p-halo-phenyl |
| Cl | 1 | p-Cl-Ph | —CH$_2$-2-indolyl |
| Cl | 1 | p-Cl-Ph | —CH$_2$-3-indolyl |
| Cl | 1 | p-Cl-Ph | —NHCO(CH$_2$)$_{0-2}$-2-indolyl |
| Cl | 1 | p-Cl-Ph | —NH(CH$_2$)$_{1-2}$-3-indolyl |
| Cl | 1 | p-Cl-Ph | NHCO-p-halo-phenyl |
| Cl | 1 | p-Cl-Ph | NHCO-m-halo-phenyl |
| Cl | 1 | p-Cl-Ph | NHCO-2-benzofuranyl |
| Cl | 1 | p-Cl-Ph | 2-(3-methylindenyl) |
| Cl | 1 | p-Cl-Ph | phenylethenyl |
| Cl | 1 | p-Cl-Ph | NHCONH-p-halo-phenyl |

TABLE 3-continued

Compounds of the formula:

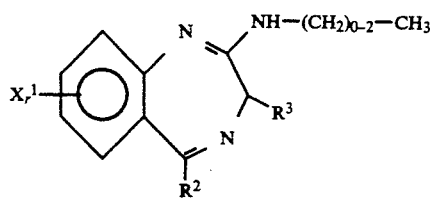

| X¹ | r | R² | R³ |
|---|---|---|---|
| Cl | 1 | Ph | —CH$_2$-2-indolyl |
| Cl | 1 | Ph | —CH$_2$-3-indolyl |
| Cl | 1 | Ph | —NHCO(CH$_2$)$_{0-2}$-2-indolyl |
| Cl | 1 | Ph | —NH(CH$_2$)$_{1-3}$-3-indolyl |
| Cl | 1 | Ph | NHCO-p-halo-phenyl |
| Cl | 1 | Ph | NHCO-m-halo-phenyl |
| Cl | 1 | Ph | NHCO-2-benzofuranyl |
| Cl | 1 | Ph | 2-(3-methylindenyl) |
| Cl | 1 | Ph | phenylethenyl |
| Cl | 1 | Ph | NHCONH-p-halo-phenyl |
| Cl | 1 | o-F-Ph | —CH$_2$-2-indolyl |
| Cl | 1 | o-F-Ph | —CH$_2$-3-indolyl |
| Cl | 1 | o-F-Ph | —NHCO(CH$_2$)$_{0-2}$-2-indolyl |
| Cl | 1 | o-F-Ph | —NH(CH$_2$)$_{1-3}$-3-indolyl |
| Cl | 1 | o-F-Ph | NHCO-p-halo-phenyl |
| Cl | 1 | o-F-Ph | NHCO-m-halo-phenyl |
| Cl | 1 | o-F-Ph | NHCO-2-benzofuranyl |
| Cl | 1 | o-F-Ph | 2-(3-methylindenyl) |
| Cl | 1 | o-F-Ph | phenylethenyl |
| Cl | 1 | o-F-Ph | NHCONH-p-halo-phenyl |
| Cl | 1 | p-F-Ph | —CH$_2$-2-indolyl |
| Cl | 1 | p-F-Ph | —CH$_2$-3-indolyl |
| Cl | 1 | p-F-Ph | —NHCO(CH$_2$)$_{0-2}$-2-indolyl |
| Cl | 1 | p-F-Ph | —NH(CH$_2$)$_{1-3}$-3-indolyl |
| Cl | 1 | p-F-Ph | NHCO-p-halo-phenyl |
| Cl | 1 | p-F-Ph | NHCO-m-halo-phenyl |
| Cl | 1 | p-F-Ph | NHCO-2-benzofuranyl |
| Cl | 1 | p-F-Ph | 2-(3-methylindenyl) |
| Cl | 1 | p-F-Ph | phenylethenyl |
| Cl | 1 | p-F-Ph | NHCONH-p-halo-phenyl |
| F | 1 | 2,4-di-Cl-Ph | —CH$_2$-2-indolyl |
| F | 1 | 2,4-di-Cl-Ph | —CH$_2$-3-indolyl |
| F | 1 | 2,4-di-Cl-Ph | —NHCO(CH$_2$)$_{0-2}$-2-indolyl |
| F | 1 | 2,4-di-Cl-Ph | —NH(CH$_2$)$_{1-3}$-3-indolyl |
| F | 1 | 2,4-di-Cl-Ph | NHCO-p-halo-phenyl |
| F | 1 | 2,4-di-Cl-Ph | NHCO-m-halo-phenyl |
| F | 1 | 2,4-di-Cl-Ph | NHCO-2-benzofuranyl |
| F | 1 | 2,4-di-Cl-Ph | 2-(3-methylindenyl) |
| F | 1 | 2,4-di-Cl-Ph | phenylethenyl |
| F | 1 | 2,4-di-Cl-Ph | NHCONH-p-halo-phenyl |
| F | 1 | 2,6-di-F-Ph | —CH$_2$-2-indolyl |
| F | 1 | 2,6-di-F-Ph | —CH$_2$-3-indolyl |
| F | 1 | 2,6-di-F-Ph | —NHCO(CH$_2$)$_{0-2}$-2-indolyl |
| F | 1 | 2,6-di-F-Ph | —NH(CH$_2$)$_{1-3}$-3-indolyl |
| F | 1 | 2,6-di-F-Ph | NHCO-p-halo-phenyl |
| F | 1 | 2,6-di-F-Ph | NHCO-m-halo-phenyl |
| F | 1 | 2,6-di-F-Ph | NHCO-2-benzofuranyl |
| F | 1 | 2,6-di-F-Ph | 2-(3-methylindenyl) |
| F | 1 | 2,6-di-F-Ph | phenylethenyl |
| F | 1 | 2,6-di-F-Ph | NHCONH-p-halo-phenyl |
| F | 1 | COO-t-butyl | —CH$_2$-2-indolyl |
| F | 1 | COO-t-butyl | —CH$_2$-3-indolyl |
| F | 1 | COO-t-butyl | —NHCO(CH$_2$)$_{0-2}$-2-indolyl |
| F | 1 | COO-t-butyl | —NH(CH$_2$)$_{1-3}$-3-indolyl |
| F | 1 | COO-t-butyl | NHCO-p-halo-phenyl |
| F | 1 | COO-t-butyl | NHCO-m-halo-phenyl |
| F | 1 | COO-t-butyl | NHCO-2-benzofuranyl |
| F | 1 | COO-t-butyl | 2-(3-methylindenyl) |
| F | 1 | COO-t-butyl | phenylethenyl |
| F | 1 | COO-t-butyl | NHCONH-p-halo-phenyl |
| F | 1 | —CH$_2$COOEt | —CH$_2$-2-indolyl |
| F | 1 | —CH$_2$COOEt | —CH$_2$-3-indolyl |
| F | 1 | —CH$_2$COOEt | —NHCO(CH$_2$)$_{0-2}$-2-indolyl |
| F | 1 | —CH$_2$COOEt | —NH(CH$_2$)$_{1-3}$-3-indolyl |
| F | 1 | —CH$_2$COOEt | NHCO-p-halo-phenyl |
| F | 1 | —CH$_2$COOEt | NHCO-m-halo-phenyl |
| F | 1 | —CH$_2$COOEt | NHCO-2-benzofuranyl |
| F | 1 | —CH$_2$COOEt | 2-(3-methylindenyl) |

TABLE 3-continued

Compounds of the formula:

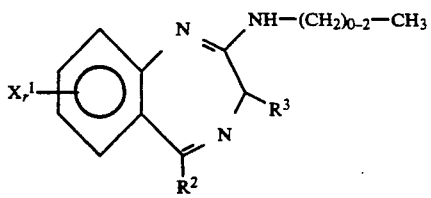

| X¹ | r | R² | R³ |
|---|---|---|---|
| F | 1 | —CH₂COOEt | phenylethenyl |
| F | 1 | —CH₂COOEt | NHCONH-p-halo-phenyl |
| CF₃ | 1 | p-Cl-Ph | —CH₂-2-indolyl |
| CF₃ | 1 | p-Cl-Ph | —CH₂-3-indolyl |
| CF₃ | 1 | p-Cl-Ph | —NHCO(CH₂)₀₋₂-2-indolyl |
| CF₃ | 1 | p-Cl-Ph | —NH(CH₂)₁₋₃-3-indolyl |
| CF₃ | 1 | p-Cl-Ph | NHCO-p-halo-phenyl |
| CF₃ | 1 | p-Cl-Ph | NHCO-m-halo-phenyl |
| CF₃ | 1 | p-Cl-Ph | NHCO-2-benzofuranyl |
| CF₃ | 1 | p-Cl-Ph | 2-(3-methylindenyl) |
| CF₃ | 1 | p-Cl-Ph | phenylethenyl |
| CF₃ | 1 | p-Cl-Ph | NHCONH-p-halo-phenyl |
| CF₃ | 1 | Ph | —CH₂-2-indolyl |
| CF₃ | 1 | Ph | —CH₂-3-indolyl |
| CF₃ | 1 | Ph | —NHCO(CH₂)₀₋₂-2-indolyl |
| CF₃ | 1 | Ph | —NH(CH₂)₁₋₃-3-indolyl |
| CF₃ | 1 | Ph | NHCO-p-halo-phenyl |
| CF₃ | 1 | Ph | NHCO-m-halo-phenyl |
| CF₃ | 1 | Ph | NHCO-2-benzofuranyl |
| CF₃ | 1 | Ph | 2-(3-methylindenyl) |
| CF₃ | 1 | Ph | phenylethenyl |
| CF₃ | 1 | Ph | NHCONH-p-halo-phenyl |
| CF₃ | 1 | o-F-Ph | —CH₂-2-indolyl |
| CF₃ | 1 | o-F-Ph | —CH₂-3-indolyl |
| CF₃ | 1 | o-F-Ph | —NHCO(CH₂)₀₋₂-2-indolyl |
| CF₃ | 1 | o-F-Ph | —NH(CH₂)₁₋₃-3-indolyl |
| CF₃ | 1 | o-F-Ph | NHCO-p-halo-phenyl |
| CF₃ | 1 | o-F-Ph | NHCO-m-halo-phenyl |
| CF₃ | 1 | o-F-Ph | NHCO-2-benzofuranyl |
| CF₃ | 1 | o-F-Ph | 2-(3-methylindenyl) |
| CF₃ | 1 | o-F-Ph | phenylethenyl |
| CF₃ | 1 | o-F-Ph | NHCONH-p-halo-phenyl |
| CF₃ | 1 | p-F-Ph | —CH₂-2-indolyl |
| CF₃ | 1 | p-F-Ph | —CH₂-3-indolyl |
| CF₃ | 1 | p-F-Ph | —NHCO(CH₂)₀₋₂-2-indolyl |
| CF₃ | 1 | p-F-Ph | —NH(CH₂)₁₋₃-3-indolyl |
| CF₃ | 1 | p-F-Ph | NHCO-p-halo-phenyl |
| CF₃ | 1 | p-F-Ph | NHCO-m-halo-phenyl |
| CF₃ | 1 | p-F-Ph | NHCO-2-benzofuranyl |
| CF₃ | 1 | p-F-Ph | 2-(3-methylindenyl) |
| CF₃ | 1 | p-F-Ph | phenylethenyl |
| CF₃ | 1 | p-F-Ph | NHCONH-p-halo-phenyl |
| NO₂ | 1 | p-Cl-Ph | —CH₂-2-indolyl |
| NO₂ | 1 | p-Cl-Ph | —CH₂-3-indolyl |
| NO₂ | 1 | p-Cl-Ph | —NHCO(CH₂)₀₋₂-2-indolyl |
| NO₂ | 1 | p-Cl-Ph | —NH(CH₂)₁₋₃-3-indolyl |
| NO₂ | 1 | p-Cl-Ph | NHCO-p-halo-phenyl |
| NO₂ | 1 | p-Cl-Ph | NHCO-m-halo-phenyl |
| NO₂ | 1 | p-Cl-Ph | NHCO-2-benzofuranyl |
| NO₂ | 1 | p-Cl-Ph | 2-(3-methylindenyl) |
| NO₂ | 1 | p-Cl-Ph | phenylethenyl |
| NO₂ | 1 | p-Cl-Ph | NHCONH-p-halo-phenyl |
| NO₂ | 1 | Ph | —CH₂-2-indolyl |
| NO₂ | 1 | Ph | —CH₂-3-indolyl |
| NO₂ | 1 | Ph | —NHCO(CH₂)₀₋₂-2-indolyl |
| NO₂ | 1 | Ph | —NH(CH₂)₁₋₃-3-indolyl |
| NO₂ | 1 | Ph | NHCO-p-halo-phenyl |
| NO₂ | 1 | Ph | NHCO-m-halo-phenyl |
| NO₂ | 1 | Ph | NHCO-2-benzofuranyl |
| NO₂ | 1 | Ph | 2-(3-methylindenyl) |
| NO₂ | 1 | Ph | phenylethenyl |
| NO₂ | 1 | Ph | NHCONH-p-halo-phenyl |
| NO₂ | 1 | o-F-Ph | —CH₂-2-indolyl |
| NO₂ | 1 | o-F-Ph | —CH₂-3-indolyl |
| NO₂ | 1 | o-F-Ph | —NHCO(CH₂)₀₋₂-2-indolyl |
| NO₂ | 1 | o-F-Ph | —NH(CH₂)₁₋₃-3-indolyl |
| NO₂ | 1 | o-F-Ph | NHCO-p-halo-phenyl |
| NO₂ | 1 | o-F-Ph | NHCO-m-halo-phenyl |

TABLE 3-continued

Compounds of the formula:

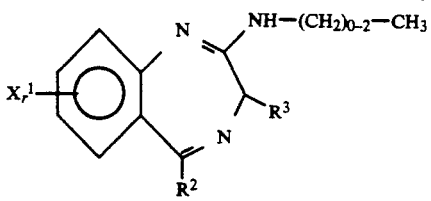

| $X^1$ | r | $R^2$ | $R^3$ |
|---|---|---|---|
| $NO_2$ | 1 | o-F-Ph | NHCO-2-benzofuranyl |
| $NO_2$ | 1 | o-F-Ph | 2-(3-methylindenyl) |
| $NO_2$ | 1 | o-F-Ph | phenylethenyl |
| $NO_2$ | 1 | o-F-Ph | NHCONH-p-halo-phenyl |
| $NO_2$ | 1 | p-F-Ph | —$CH_2$-2-indolyl |
| $NO_2$ | 1 | p-F-Ph | —$CH_2$-3-indolyl |
| $NO_2$ | 1 | p-F-Ph | —$NHCO(CH_2)_{0-2}$-2-indolyl |
| $NO_2$ | 1 | p-F-Ph | —$NH(CH_2)_{1-3}$-3-indolyl |
| $NO_2$ | 1 | p-F-Ph | NHCO-p-halo-phenyl |
| $NO_2$ | 1 | p-F-Ph | NHCO-m-halo-phenyl |
| $NO_2$ | 1 | p-F-Ph | NHCO-2-benzofuranyl |
| $NO_2$ | 1 | p-F-Ph | 2-(3-methylindenyl) |
| $NO_2$ | 1 | p-F-Ph | phenylethenyl |
| $NO_2$ | 1 | p-F-Ph | NHCONH-p-halo-phenyl |
| $CH_3$ | 1 | phenyl | —$CH_2$-2-indolyl |
| $CH_3$ | 1 | phenyl | —$CH_2$-3-indolyl |
| $CH_3$ | 1 | phenyl | —$NHCO(CH_2)_{0-2}$-2-indolyl |
| $CH_3$ | 1 | phenyl | —$NH(CH_2)_{1-3}$-3-indolyl |
| $CH_3$ | 1 | phenyl | NHCO-p-halo-phenyl |
| $CH_3$ | 1 | phenyl | NHCO-m-halo-phenyl |
| $CH_3$ | 1 | phenyl | NHCO-2-benzofuranyl |
| $CH_3$ | 1 | phenyl | 2-(3-methylindenyl) |
| $CH_3$ | 1 | phenyl | phenylethenyl |
| $CH_3$ | 1 | phenyl | NHCONH-p-halo-phenyl |
| H | 1 | o-F-Ph | —$CH_2$-2-indolyl |
| H | 1 | o-F-Ph | —$CH_2$-3-indolyl |
| H | 1 | o-F-Ph | —$NHCO(CH_2)_{0-2}$-2-indolyl |
| H | 1 | o-F-Ph | —$NH(CH_2)_{1-3}$-3-indolyl |
| H | 1 | o-F-Ph | NHCO-p-halo-phenyl |
| H | 1 | o-F-Ph | NHCO-m-halo-phenyl |
| H | 1 | o-F-Ph | NHCO-2-benzofuranyl |
| H | 1 | o-F-Ph | 2-(3-methylindenyl) |
| H | 1 | o-F-Ph | phenylethenyl |
| H | 1 | o-F-Ph | NHCONH-p-halo-phenyl |
| H | 1 | p-Cl-Ph | —$CH_2$-2-indolyl |
| H | 1 | p-Cl-Ph | —$CH_2$-3-indolyl |
| H | 1 | p-Cl-Ph | —$NHCO(CH_2)_{0-2}$-2-indolyl |
| H | 1 | p-Cl-Ph | —$NH(CH_2)_{1-3}$-3-indolyl |
| H | 1 | p-Cl-Ph | NHCO-p-halo-phenyl |
| H | 1 | p-Cl-Ph | NHCO-m-halo-phenyl |
| H | 1 | p-Cl-Ph | NHCO-2-benzofuranyl |
| H | 1 | p-Cl-Ph | 2-(3-methylindenyl) |
| H | 1 | p-Cl-Ph | phenylethenyl |
| H | 1 | p-Cl-Ph | NHCONH-p-halo-phenyl |
| H | 1 | o-F-Ph | $CH_2$-2 or 3-(1-methyl indolyl) |
| H | 1 | —$CH_2$COO-t-butyl | $CH_2$-2 or 3-(1-methyl indolyl) |
| H | 1 | —$CH_2$COOEt | $CH_2$-2 or 3-(1-methyl indolyl) |
| H | 1 | Ph | $CH_2$-2 or 3-(1-methyl indolyl) |
| H | 1 | o-F-Ph | $NHCO(CH_2)_{0-2}$-2-indolyl |
| H | 1 | —$CH_2$COO-t-butyl | $NHCO(CH_2)_{0-2}$-2-indolyl |
| H | 1 | —$CH_2$COOEt | $NHCO(CH_2)_{0-2}$-2-indolyl |
| H | 1 | Ph | $NHCO(CH_2)_{0-2}$-2-indolyl |
| H | 1 | o-F-Ph | $NHCO(CH_2)_{0-2}$-2 or 3-(1-methylindolyl) |
| H | 1 | $CH_2$COO-t-butyl | $NHCO(CH_2)_{0-2}$-2 or 3-(1-methylindolyl) |
| H | 1 | —$CH_2$COOEt | $NHCO(CH_2)_{0-2}$-2 or 3-(1-methylindolyl) |
| H | 1 | Ph | $NHCO(CH_2)_{0-2}$-2 or 3-(1-methylindolyl) |
| H | 1 | o-F-Ph | $NH(CH_2)_{1-3}$-2-indolyl |
| H | 1 | —$CH_2$COO-t-butyl | $NH(CH_2)_{1-3}$-2-indolyl |
| H | 1 | —$CH_2$COOEt | $NH(CH_2)_{1-3}$-2-indolyl |
| H | 1 | Ph | $NH(CH_2)_{1-3}$-2-indolyl |
| H | 1 | o-F-Ph | $NH(CH_2)_{1-3}$-2 or 3-(1-methylindolyl) |
| H | 1 | —$CH_2$COO-t-butyl | $NH(CH_2)_{1-3}$-2 or 3-(1-methylindolyl) |
| H | 1 | —$CH_2$COOEt | $NH(CH_2)_{1-3}$-2 or 3-(1-methylindolyl) |
| H | 1 | Ph | $NH(CH_2)_{1-3}$-2 or 3-(1-methylindolyl) |

TABLE 3-continued

Compounds of the formula:

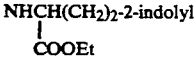

| X¹ | r | R² | R³ |
|----|---|-----|-----|
| H | 1 | o-F-Ph | NHCH(CH₂)₂-2-indolyl<br>\|<br>COOEt |
| H | 1 | —CH₂COO-t-butyl | NHCH(CH₂)₂-2-indolyl<br>\|<br>COOEt |
| H | 1 | —CH₂COOEt | NHCH(CH₂)₂-2-indolyl<br>\|<br>COOEt |
| H | 1 | Ph | NHCH(CH₂)₂-2-indolyl<br>\|<br>COOEt |
| H | 1 | o-F-Ph | COOEt<br>\|<br>NHCH(CH₂)₂-2 or 3-(1-methylindolyl) |
| H | 1 | —CH₂COO-t-butyl | COOEt<br>\|<br>NHCH(CH₂)₂-2 or 3-(1-methylindolyl) |
| H | 1 | —CH₂COOEt | COOEt<br>\|<br>NHCH(CH₂)₂-2 or 3-(1-methylindolyl) |
| H | 1 | Ph | COOEt<br>\|<br>NHCH(CH₂)₂-2 or 3-(1-methylindolyl) |
| H | 1 | o-F-Ph | NHCH(CH₂)₂-2 or 3-indolyl-<br>\|<br>COO-t-Butyl |
| H | 1 | —CH₂COO-t-butyl | NHCH(CH₂)₂-2 or 3-indolyl-<br>\|<br>COO-t-Butyl |
| H | 1 | —CH₂COOEt | NHCH(CH₂)₂-2 or 3-indolyl-<br>\|<br>COO-t-Butyl |
| H | 1 | Ph | NHCH(CH₂)₂-2 or 3-indolyl-<br>\|<br>COO-t-Butyl |
| H | 1 | o-F-Ph | COO-t-Butyl<br>\|<br>NHCH(CH₂)₂-2 or 3-(1-methylindolyl) |
| H | 1 | —CH₂COO-t-butyl | COO-t-Butyl<br>\|<br>NHCH(CH₂)₂-2 or 3-(1-methylindolyl) |
| H | 1 | —CH₂COOEt | COO-t-Butyl<br>\|<br>NHCH(CH₂)₂-2 or 3-(1-methylindolyl) |
| H | 1 | Ph | COO-t-Butyl<br>\|<br>NHCH(CH₂)₂-2 or 3-(1-methylindolyl) |

TABLE 4

Compounds of the formula:

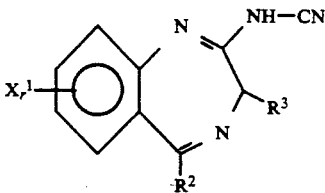 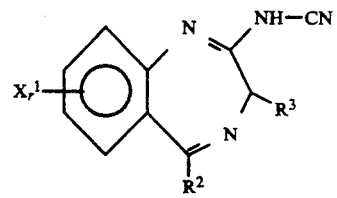

| X¹ | r | R² | R³ |
|---|---|---|---|
| H | 1 | o-F-Ph | —CH$_2$-2-indolyl |
| H | 1 | o-F-Ph | —CH$_2$-3-indolyl |
| H | 1 | o-F-Ph | NH(CH$_2$)$_{1-3}$-3-indolyl |
| H | 1 | o-F-Ph | —NHCH$_2$—(CH$_2$)$_2$-3-indolyl<br>\|<br>COOEt |
| H | 1 | o-F-Ph | —CH$_2$NH(CH$_2$)$_2$-3-indolyl |
| H | 1 | o-F-Ph | —NHCO—(CH$_2$)$_{0-2}$-2-indolyl |
| H | 1 | o-F-Ph | —NHCO(CH$_2$)$_{0-2}$-3-indolyl |
| H | 1 | o-F-Ph | NHCO-p-halo-phenyl |
| H | 1 | o-F-Ph | NHCO-m-halo-phenyl |
| H | 1 | o-F-Ph | NHCO-2-benzofuranyl |
| H | 1 | o-F-Ph | 2-(3-methylindenyl) |
| H | 1 | o-F-Ph | phenylethenyl |
| H | 1 | o-F-Ph | NHCONH-p-halo-phenyl |
| H | 1 | p-Cl-Ph | —CH$_2$-2-indolyl |
| H | 1 | p-Cl-Ph | —CH$_2$-3-indolyl |
| H | 1 | p-Cl-Ph | —NH(CH$_2$)$_{1-3}$-3-indolyl |
| H | 1 | p-Cl-Ph | —NHCO—(CH$_2$)$_{0-2}$-2-indolyl |
| H | 1 | p-Cl-Ph | NHCO-p-halo-phenyl |
| H | 1 | p-Cl-Ph | NHCO-m-halo-phenyl |
| H | 1 | p-Cl-Ph | NHCO-2-benzofuranyl |
| H | 1 | p-Cl-Ph | 2-(3-methylindenyl) |
| H | 1 | p-Cl-Ph | phenylethenyl |
| H | 1 | p-Cl-Ph | NHCONH-p-halo-phenyl |
| H | 1 | phenyl | —CH$_2$-2-indolyl |
| H | 1 | phenyl | —CH$_2$-3-indolyl |
| H | 1 | phenyl | —NHCO(CH$_2$)$_{0-2}$-3-indolyl |
| H | 1 | phenyl | —NH(CH$_2$)$_{1-3}$-3-indolyl |
| H | 1 | phenyl | NHCO-p-halo-phenyl |
| H | 1 | phenyl | NHCO-m-halo-phenyl |
| H | 1 | phenyl | NHCO-2-benzofuranyl |
| H | 1 | phenyl | 2-(3-methylindenyl) |
| H | 1 | phenyl | phenylethenyl |
| H | 1 | phenyl | NHCONH-p-halo-phenyl |
| H | 1 | p-F-Ph | —CH$_2$-2-indolyl |
| H | 1 | p-F-Ph | —CH$_2$-3-indolyl |
| H | 1 | p-F-Ph | —NHCO(CH$_2$)$_{0-2}$-2-indolyl |
| H | 1 | p-F-Ph | —NH(CH$_2$)$_{1-3}$-3-indolyl |
| H | 1 | p-F-Ph | NHCO-p-halo-phenyl |
| H | 1 | p-F-Ph | NHCO-m-halo-phenyl |
| H | 1 | p-F-Ph | NHCO-2-benzofuranyl |
| H | 1 | p-F-Ph | 2-(3-methylindenyl) |
| H | 1 | p-F-Ph | phenylethenyl |
| H | 1 | p-F-Ph | NHCONH-p-halo-phenyl |
| H | 1 | 2,4-di-Cl-Ph | —CH$_2$-2-indolyl |
| H | 1 | 2,4-di-Cl-Ph | —CH$_2$-3-indolyl |
| H | 1 | 2,4-di-Cl-Ph | —NHCO(CH$_2$)$_{0-2}$-2-indolyl |
| H | 1 | 2,4-di-Cl-Ph | —NH(CH$_2$)$_{1-3}$-3-indolyl |
| H | 1 | 2,4-di-Cl-Ph | NHCO-p-halo-phenyl |
| H | 1 | 2,4-di-Cl-Ph | NHCO-m-halo-phenyl |
| H | 1 | 2,4-di-Cl-Ph | NHCO-2-benzofuranyl |
| H | 1 | 2,4-di-Cl-Ph | 2-(3-methylindenyl) |
| H | 1 | 2,4-di-Cl-Ph | phenylethenyl |
| H | 1 | 2,4-di-Cl-Ph | NHCONH-p-halo-phenyl |
| H | 1 | 2,6-di-F-Ph | —CH$_2$-2-indolyl |
| H | 1 | 2,6-di-F-Ph | —CH$_2$-3-indolyl |
| H | 1 | 2,6-di-F-Ph | —NHCO(CH$_2$)$_{0-2}$-2-indolyl |
| H | 1 | 2,6-di-F-Ph | —NH(CH$_2$)$_{1-3}$-3-indolyl |
| H | 1 | 2,6-di-F-Ph | NHCO-p-halo-phenyl |
| H | 1 | 2,6-di-F-Ph | NHCO-m-halo-phenyl |
| H | 1 | 2,6-di-F-Ph | NHCO-2-benzofuranyl |
| H | 1 | 2,6-di-F-Ph | 2-(3-methylindenyl) |
| H | 1 | 2,6-di-F-Ph | phenylethenyl |
| H | 1 | 2,6-di-F-Ph | NHCONH-p-halo-phenyl |
| H | 1 | CH$_2$COO-t-butyl | —CH$_2$-2-indolyl |
| H | 1 | CH$_2$COO-t-butyl | —CH$_2$-3-indolyl |
| H | 1 | CH$_2$COO-t-butyl | —NHCO(CH$_2$)$_{0-2}$-3-indolyl |
| H | 1 | CH$_2$COO-t-butyl | —NH(CH$_2$)$_{1-3}$-3-indolyl |
| H | 1 | CH$_2$COO-t-butyl | NHCO-p-halo-phenyl |
| H | 1 | CH$_2$COO-t-butyl | NHCO-m-halo-phenyl |
| H | 1 | CH$_2$COO-t-butyl | NHCO-2-benzofuranyl |
| H | 1 | CH$_2$COO-t-butyl | 2-(3-methylindenyl) |
| H | 1 | CH$_2$COO-t-butyl | phenylethenyl |
| H | 1 | CH$_2$COO-t-butyl | NHCONH-p-halo-phenyl |
| H | 1 | —CH$_2$COOEt | —CH$_2$-2-indolyl |
| H | 1 | —CH$_2$COOEt | —CH$_2$-3-indolyl |
| H | 1 | —CH$_2$COOEt | —NHCO(CH$_2$)$_{0-2}$-3-indolyl |
| H | 1 | —CH$_2$COOEt | —NH(CH$_2$)$_{1-3}$-3-indolyl |
| H | 1 | —CH$_2$COOEt | NHCO-p-halo-phenyl |
| H | 1 | —CH$_2$COOEt | NHCO-m-halo-phenyl |
| H | 1 | —CH$_2$COOEt | NHCO-2-benzofuranyl |
| H | 1 | —CH$_2$COOEt | 2-(3-methylindenyl) |
| H | 1 | —CH$_2$COOEt | phenylethenyl |
| H | 1 | —CH$_2$COOEt | NHCONH-p-halo-phenyl |
| Cl | 1 | p-Cl-Ph | —CH$_2$-2-indolyl |
| Cl | 1 | p-Cl-Ph | —CH$_2$-3-indolyl |
| Cl | 1 | p-Cl-Ph | —NHCO(CH$_2$)$_{0-2}$-2-indolyl |
| Cl | 1 | p-Cl-Ph | —NH(CH$_2$)$_{1-3}$-3-indolyl |
| Cl | 1 | p-Cl-Ph | NHCO-p-halo-phenyl |
| Cl | 1 | p-Cl-Ph | NHCO-m-halo-phenyl |
| Cl | 1 | p-Cl-Ph | NHCO-2-benzofuranyl |
| Cl | 1 | p-Cl-Ph | 2-(3-methylindenyl) |
| Cl | 1 | p-Cl-Ph | phenylethenyl |
| Cl | 1 | p-Cl-Ph | NHCONH-p-halo-phenyl |
| Cl | 1 | Ph | —CH$_2$-2-indolyl |
| Cl | 1 | Ph | —CH$_2$-3-indolyl |
| Cl | 1 | Ph | —NHCO(CH$_2$)$_{0-2}$-2-indolyl |
| Cl | 1 | Ph | —NH(CH$_2$)$_{1-3}$-3-indolyl |
| Cl | 1 | Ph | NHCO-p-halo-phenyl |
| Cl | 1 | Ph | NHCO-m-halo-phenyl |
| Cl | 1 | Ph | NHCO-2-benzofuranyl |
| Cl | 1 | Ph | 2-(3-methylindenyl) |
| Cl | 1 | Ph | phenylethenyl |
| Cl | 1 | Ph | NHCONH-p-halo-phenyl |
| Cl | 1 | o-F-Ph | —CH$_2$-2-indolyl |
| Cl | 1 | o-F-Ph | —CH$_2$-3-indolyl |
| Cl | 1 | o-F-Ph | —NHCO(CH$_2$)$_{0-2}$-2-indolyl |
| Cl | 1 | o-F-Ph | —NH(CH$_2$)$_{1-3}$-3-indolyl |
| Cl | 1 | o-F-Ph | NHCO-p-halo-phenyl |
| Cl | 1 | o-F-Ph | NHCO-m-halo-phenyl |
| Cl | 1 | o-F-Ph | NHCO-2-benzofuranyl |
| Cl | 1 | o-F-Ph | 2-(3-methylindenyl) |
| Cl | 1 | o-F-Ph | phenylethenyl |
| Cl | 1 | o-F-Ph | NHCONH-p-halo-phenyl |
| Cl | 1 | p-F-Ph | —CH$_2$-2-indolyl |
| Cl | 1 | p-F-Ph | —CH$_2$-3-indolyl |
| Cl | 1 | p-F-Ph | —NHCO(CH$_2$)$_{0-2}$-2-indolyl |
| Cl | 1 | p-F-Ph | —NH(CH$_2$)$_{1-3}$-3-indolyl |
| Cl | 1 | p-F-Ph | NHCO-p-halo-phenyl |
| Cl | 1 | p-F-Ph | NHCO-m-halo-phenyl |
| Cl | 1 | p-F-Ph | NHCO-2-benzofuranyl |
| Cl | 1 | p-F-Ph | 2-(3-methylindenyl) |
| Cl | 1 | p-F-Ph | phenylethenyl |
| Cl | 1 | p-F-Ph | NHCONH-p-halo-phenyl |
| F | 1 | 2,4-di-Cl-Ph | —CH$_2$-2-indolyl |
| F | 1 | 2,4-di-Cl-Ph | —CH$_2$-3-indolyl |
| F | 1 | 2,4-di-Cl-Ph | —NHCO(CH$_2$)$_{0-2}$-2-indolyl |
| F | 1 | 2,4-di-Cl-Ph | —NH(CH$_2$)$_{1-3}$-3-indolyl |
| F | 1 | 2,4-di-Cl-Ph | NHCO-p-halo-phenyl |
| F | 1 | 2,4-di-Cl-Ph | NHCO-m-halo-phenyl |
| F | 1 | 2,4-di-Cl-Ph | NHCO-2-benzofuranyl |
| F | 1 | 2,4-di-Cl-Ph | 2-(3-methylindenyl) |
| F | 1 | 2,4-di-Cl-Ph | phenylethenyl |
| F | 1 | 2,4-di-Cl-Ph | NHCONH-p-halo-phenyl |

TABLE 4-continued

Compounds of the formula:

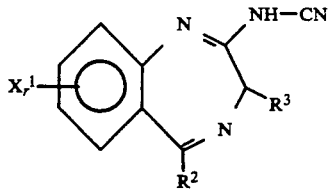

| X¹ | r | R² | R³ |
|---|---|---|---|
| F | 1 | 2,6-di-F-Ph | —CH$_2$-2-indolyl |
| F | 1 | 2,6-di-F-Ph | —CH$_2$-3-indolyl |
| F | 1 | 2,6-di-F-Ph | —NHCO(CH$_2$)$_{0-2}$-2-indolyl |
| F | 1 | 2,6-di-F-Ph | —NH(CH$_2$)$_{1-3}$-3-indolyl |
| F | 1 | 2,6-di-F-Ph | NHCO-p-halo-phenyl |
| F | 1 | 2,6-di-F-Ph | NHCO-m-halo-phenyl |
| F | 1 | 2,6-di-F-Ph | NHCO-2-benzofuranyl |
| F | 1 | 2,6-di-F-Ph | 2-(3-methylindenyl) |
| F | 1 | 2,6-di-F-Ph | phenylethenyl |
| F | 1 | 2,6-di-F-Ph | NHCONH-p-halo-phenyl |
| F | 1 | COO-t-butyl | —CH$_2$-2-indolyl |
| F | 1 | COO-t-butyl | —CH$_2$-3-indolyl |
| F | 1 | COO-t-butyl | —NHCO(CH$_2$)$_{0-2}$-2-indolyl |
| F | 1 | COO-t-butyl | —NH(CH$_2$)$_{1-3}$-3-indolyl |
| F | 1 | COO-t-butyl | NHCO-p-halo-phenyl |
| F | 1 | COO-t-butyl | NHCO-m-halo-phenyl |
| F | 1 | COO-t-butyl | NHCO-2-benzofuranyl |
| F | 1 | COO-t-butyl | 2-(3-methylindenyl) |
| F | 1 | COO-t-butyl | phenylethenyl |
| F | 1 | COO-t-butyl | NHCONH-p-halo-phenyl |
| F | 1 | —CH$_2$COOEt | —CH$_2$-2-indolyl |
| F | 1 | —CH$_2$COOEt | —CH$_2$-3-indolyl |
| F | 1 | —CH$_2$COOEt | —NHCO(CH$_2$)$_{0-2}$-2-indolyl |
| F | 1 | —CH$_2$COOEt | —NH(CH$_2$)$_{1-3}$-3-indolyl |
| F | 1 | —CH$_2$COOEt | NHCO-p-halo-phenyl |
| F | 1 | —CH$_2$COOEt | NHCO-m-halo-phenyl |
| F | 1 | —CH$_2$COOEt | NHCO-2-benzofuranyl |
| F | 1 | —CH$_2$COOEt | 2-(3-methylindenyl) |
| F | 1 | —CH$_2$COOEt | phenylethenyl |
| F | 1 | —CH$_2$COOEt | NHCONH-p-halo-phenyl |
| CF$_3$ | 1 | p-Cl-Ph | —CH$_2$-2-indolyl |
| CF$_3$ | 1 | p-Cl-Ph | —CH$_2$-3-indolyl |
| CF$_3$ | 1 | p-Cl-Ph | —NHCO(CH$_2$)$_{0-2}$-2-indolyl |
| CF$_3$ | 1 | p-Cl-Ph | —NH(CH$_2$)$_{1-3}$-3-indolyl |
| CF$_3$ | 1 | p-Cl-Ph | NHCO-p-halo-phenyl |
| CF$_3$ | 1 | p-Cl-Ph | NHCO-m-halo-phenyl |
| CF$_3$ | 1 | p-Cl-Ph | NHCO-2-benzofuranyl |
| CF$_3$ | 1 | p-Cl-Ph | 2-(3-methylindenyl) |
| CF$_3$ | 1 | p-Cl-Ph | phenylethenyl |
| CF$_3$ | 1 | p-Cl-Ph | NHCONH-p-halo-phenyl |
| CF$_3$ | 1 | Ph | —CH$_2$-2-indolyl |
| CF$_3$ | 1 | Ph | —CH$_2$-3-indolyl |
| CF$_3$ | 1 | Ph | —NHCO(CH$_2$)$_{0-2}$-2-indolyl |
| CF$_3$ | 1 | Ph | —NH(CH$_2$)$_{1-3}$-3-indolyl |
| CF$_3$ | 1 | Ph | NHCO-p-halo-phenyl |
| CF$_3$ | 1 | Ph | NHCO-m-halo-phenyl |
| CF$_3$ | 1 | Ph | NHCO-2-benzofuranyl |
| CF$_3$ | 1 | Ph | 2-(3-methylindenyl) |
| CF$_3$ | 1 | Ph | phenylethenyl |
| CF$_3$ | 1 | Ph | NHCONH-p-halo-phenyl |
| CF$_3$ | 1 | o-F-Ph | —CH$_2$-2-indolyl |
| CF$_3$ | 1 | o-F-Ph | —CH$_2$-3-indolyl |
| CF$_3$ | 1 | o-F-Ph | NHCO(CH$_2$)$_{0-2}$-2-indolyl |
| CF$_3$ | 1 | o-F-Ph | NH(CH$_2$)$_{1-3}$-3-indolyl |
| CF$_3$ | 1 | o-F-Ph | NHCO-p-halo-phenyl |
| CF$_3$ | 1 | o-F-Ph | NHCO-m-halo-phenyl |
| CF$_3$ | 1 | o-F-Ph | NHCO-2-benzofuranyl |
| CF$_3$ | 1 | o-F-Ph | 2-(3-methylindenyl) |
| CF$_3$ | 1 | o-F-Ph | phenylethenyl |
| CF$_3$ | 1 | o-F-Ph | NHCONH-p-halo-phenyl |
| CF$_3$ | 1 | p-F-Ph | —CH$_2$-2-indolyl |
| CF$_3$ | 1 | p-F-Ph | —CH$_2$-3-indolyl |
| CF$_3$ | 1 | p-F-Ph | —NHCO(CH$_2$)$_{0-2}$-2-indolyl |
| CF$_3$ | 1 | p-F-Ph | —NH(CH$_2$)$_{1-3}$-3-indolyl |
| CF$_3$ | 1 | p-F-Ph | NHCO-p-halo-phenyl |
| CF$_3$ | 1 | p-F-Ph | NHCO-m-halo-phenyl |
| CF$_3$ | 1 | p-F-Ph | NHCO-2-benzofuranyl |
| CF$_3$ | 1 | p-F-Ph | 2-(3-methylindenyl) |
| CF$_3$ | 1 | p-F-Ph | phenylethenyl |

TABLE 4-continued

Compounds of the formula:

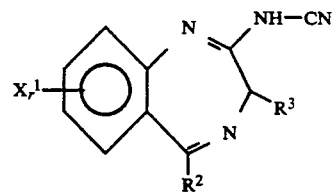

| X¹ | r | R² | R³ |
|---|---|---|---|
| CF$_3$ | 1 | p-F-Ph | NHCONH-p-halo-phenyl |
| NO$_2$ | 1 | p-Cl-Ph | —CH$_2$-2-indolyl |
| NO$_2$ | 1 | p-Cl-Ph | —CH$_2$-3-indolyl |
| NO$_2$ | 1 | p-Cl-Ph | —NHCO(CH$_2$)$_{0-2}$-2-indolyl |
| NO$_2$ | 1 | p-Cl-Ph | —NH(CH$_2$)$_{1-3}$-3-indolyl |
| NO$_2$ | 1 | p-Cl-Ph | NHCO-p-halo-phenyl |
| NO$_2$ | 1 | p-Cl-Ph | NHCO-m-halo-phenyl |
| NO$_2$ | 1 | p-Cl-Ph | NHCO-2-benzofuranyl |
| NO$_2$ | 1 | p-Cl-Ph | 2-(3-methylindenyl) |
| NO$_2$ | 1 | p-Cl-Ph | phenylethenyl |
| NO$_2$ | 1 | p-Cl-Ph | NHCONH-p-halo-phenyl |
| NO$_2$ | 1 | Ph | —CH$_2$-2-indolyl |
| NO$_2$ | 1 | Ph | —CH$_2$-3-indolyl |
| NO$_2$ | 1 | Ph | —NHCO(CH$_2$)$_{0-2}$-2-indolyl |
| NO$_2$ | 1 | Ph | —NH(CH$_2$)$_{1-3}$-3-indolyl |
| NO$_2$ | 1 | Ph | NHCO-p-halo-phenyl |
| NO$_2$ | 1 | Ph | NHCO-m-halo-phenyl |
| NO$_2$ | 1 | Ph | NHCO-2-benzofuranyl |
| NO$_2$ | 1 | Ph | 2-(3-methylindenyl) |
| NO$_2$ | 1 | Ph | phenylethenyl |
| NO$_2$ | 1 | Ph | NHCONH-p-halo-phenyl |
| NO$_2$ | 1 | o-F-Ph | —CH$_2$-2-indolyl |
| NO$_2$ | 1 | o-F-Ph | —CH$_2$-3-indolyl |
| NO$_2$ | 1 | o-F-Ph | —NHCO(CH$_2$)$_{0-2}$-2-indolyl |
| NO$_2$ | 1 | o-F-Ph | —NH(CH$_2$)$_{1-3}$-3-indolyl |
| NO$_2$ | 1 | o-F-Ph | NHCO-p-halo-phenyl |
| NO$_2$ | 1 | o-F-Ph | NHCO-m-halo-phenyl |
| NO$_2$ | 1 | o-F-Ph | NHCO-2-benzofuranyl |
| NO$_2$ | 1 | o-F-Ph | 2-(3-methylindenyl) |
| NO$_2$ | 1 | o-F-Ph | phenylethenyl |
| NO$_2$ | 1 | o-F-Ph | NHCONH-p-halo-phenyl |
| NO$_2$ | 1 | p-F-Ph | —CH$_2$-2-indolyl |
| NO$_2$ | 1 | p-F-Ph | —CH$_2$-3-indolyl |
| NO$_2$ | 1 | p-F-Ph | —NHCO(CH$_2$)$_{0-2}$-2-indolyl |
| NO$_2$ | 1 | p-F-Ph | —NH(CH$_2$)$_{1-3}$-3-indolyl |
| NO$_2$ | 1 | p-F-Ph | NHCO-p-halo-phenyl |
| NO$_2$ | 1 | p-F-Ph | NHCO-m-halo-phenyl |
| NO$_2$ | 1 | p-F-Ph | NHCO-2-benzofuranyl |
| NO$_2$ | 1 | p-F-Ph | 2-(3-methylindenyl) |
| NO$_2$ | 1 | p-F-Ph | phenylethenyl |
| NO$_2$ | 1 | p-F-Ph | NHCONH-p-halo-phenyl |
| CH$_3$ | 1 | phenyl | —CH$_2$-2-indolyl |
| CH$_3$ | 1 | phenyl | —CH$_2$-3-indolyl |
| CH$_3$ | 1 | phenyl | —NHCO(CH$_2$)$_{0-2}$-2-indolyl |
| CH$_3$ | 1 | phenyl | —NH(CH$_2$)$_{1-3}$-3-indolyl |
| CH$_3$ | 1 | phenyl | NHCO-p-halo-phenyl |
| CH$_3$ | 1 | phenyl | NHCO-m-halo-phenyl |
| CH$_3$ | 1 | phenyl | NHCO-2-benzofuranyl |
| CH$_3$ | 1 | phenyl | 2-(3-methylindenyl) |
| CH$_3$ | 1 | phenyl | phenylethenyl |
| CH$_3$ | 1 | phenyl | NHCONH-p-halo-phenyl |
| H | 1 | o-F-Ph | —CH$_2$-2-indolyl |
| H | 1 | o-F-Ph | —CH$_2$-3-indolyl |
| H | 1 | o-F-Ph | —NHCO(CH$_2$)$_{0-2}$-2-indolyl |
| H | 1 | o-F-Ph | —NH(CH$_2$)$_{1-3}$-3-indolyl |
| H | 1 | o-F-Ph | NHCO-p-halo-phenyl |
| H | 1 | o-F-Ph | NHCO-m-halo-phenyl |
| H | 1 | o-F-Ph | NHCO-2-benzofuranyl |
| H | 1 | o-F-Ph | 2-(3-methylindenyl) |
| H | 1 | o-F-Ph | phenylethenyl |
| H | 1 | o-F-Ph | NHCONH-p-halo-phenyl |
| H | 1 | p-Cl-Ph | —CH$_2$-2-indolyl |
| H | 1 | p-Cl-Ph | —CH$_2$-3-indolyl |
| H | 1 | p-Cl-Ph | —NHCO(CH$_2$)$_{0-2}$-2-indolyl |
| H | 1 | p-Cl-Ph | —NH(CH$_2$)$_{1-3}$-3-indolyl |
| H | 1 | p-Cl-Ph | NHCO-p-halo-phenyl |
| H | 1 | p-Cl-Ph | NHCO-m-halo-phenyl |
| H | 1 | p-Cl-Ph | NHCO-2-benzofuranyl |
| H | 1 | p-Cl-Ph | 2-(3-methylindenyl) |

TABLE 4-continued

Compounds of the formula:

| $X^1_r$ | r | $R^2$ | $R^3$ |
|---|---|---|---|
| H | 1 | p-Cl-Ph | phenylethenyl |
| H | 1 | p-Cl-Ph | NHCONH-p-halo-phenyl |
| H | 1 | o-F-Ph | CH$_2$-2 or 3-(1-methylindolyl) |
| H | 1 | —CH$_2$COO-t-butyl | CH$_2$-2 or 3-(1-methylindolyl) |
| H | 1 | —CH$_2$COOEt | CH$_2$-2 or 3-(1-methylindolyl) |
| H | 1 | Ph | CH$_2$-2 or 3-(1-methylindolyl) |
| H | 1 | o-F-Ph | NHCO(CH$_2$)$_{0-2}$-2-indolyl |
| H | 1 | —CH$_2$COO-t-butyl | NHCO(CH$_2$)$_{0-2}$-2-indolyl |
| H | 1 | —CH$_2$COOEt | NHCO(CH$_2$)$_{0-2}$-2-indolyl |
| H | 1 | Ph | NHCO(CH$_2$)$_{0-2}$-2-indolyl |
| H | 1 | o-F-Ph | NHCO(CH$_2$)$_{0-2}$-2 or 3-(1-methylindolyl) |
| H | 1 | —CH$_2$COO-t-butyl | NHCO(CH$_2$)$_{0-2}$-2 or 3-(1-methylindolyl) |
| H | 1 | —CH$_2$COOEt | NHCO(CH$_2$)$_{0-2}$-2 or 3-(1-methylindolyl) |
| H | 1 | Ph | NHCO(CH$_2$)$_{0-2}$-2 or 3-(1-methylindolyl) |
| H | 1 | o-F-Ph | NH(CH$_2$)$_{1-3}$-2-indolyl |
| H | 1 | —CH$_2$COO-t-butyl | NH(CH$_2$)$_{1-3}$-2-indolyl |
| H | 1 | —CH$_2$COOEt | NH(CH$_2$)$_{1-3}$-2-indolyl |
| H | 1 | Ph | NH(CH$_2$)$_{1-3}$-2-indolyl |
| H | 1 | o-F-Ph | NH(CH$_2$)$_{1-3}$-2 or 3-(1-methylindolyl) |
| H | 1 | —CH$_2$COO-t-butyl | NH(CH$_2$)$_{1-3}$-2 or 3-(1-methylindolyl) |
| H | 1 | —CH$_2$COOEt | NH(CH$_2$)$_{1-3}$-2 or 3-(1-methylindolyl) |
| H | 1 | Ph | NH(CH$_2$)$_{1-3}$-2 or 3-(1-methylindolyl) |
| H | 1 | o-F-Ph | NHCH(CH$_2$)$_2$-2-indolyl<br>\|<br>COOEt |
| H | 1 | —CH$_2$COO-t-butyl | NHCH(CH$_2$)$_2$-2-indolyl<br>\|<br>COOEt |
| H | 1 | —CH$_2$COOEt | NHCH(CH$_2$)$_2$-2-indolyl<br>\|<br>COOEt |
| H | 1 | Ph | NHCH(CH$_2$)$_2$-2-indolyl<br>\|<br>COOEt |
| H | 1 | o-F-Ph | COOEt<br>\|<br>NHCH(CH$_2$)$_2$-2 or 3-(1-methylindolyl) |
| H | 1 | —CH$_2$COO-t-butyl | COOEt<br>\|<br>NHCH(CH$_2$)$_2$-2 or 3-(1-methylindolyl) |
| H | 1 | —CH$_2$COOEt | COOEt<br>\|<br>NHCH(CH$_2$)$_2$-2 or 3-(1-methylindolyl) |
| H | 1 | Ph | COOEt<br>\|<br>NHCH(CH$_2$)$_2$-2 or 3-(1-methylindolyl) |
| H | 1 | o-F-Ph | NHCH(CH$_2$)$_2$-2 or 3-indolyl-<br>\|<br>COO-t-Butyl |
| H | 1 | —CH$_2$COO-t-butyl | NHCH(CH$_2$)$_2$-2 or 3-indolyl-<br>\|<br>COO-t-Butyl |
| H | 1 | —CH$_2$COOEt | NHCH(CH$_2$)$_2$-2 or 3-indolyl-<br>\|<br>COO-t-Butyl |
| H | 1 | Ph | NHCH(CH$_2$)$_2$-2 or 3-indolyl-<br>\|<br>COO-t-Butyl |
| H | 1 | o-F-Ph | COO-t-Butyl<br>\|<br>NHCH(CH$_2$)$_2$-2 or 3-(1-methylindolyl) |
| H | 1 | —CH$_2$COO-t-butyl | COO-t-Butyl<br>\|<br>NHCH(CH$_2$)$_2$-2 or 3-(1-methylindolyl) |
| H | 1 | —CH$_2$COOEt | COO-t-Butyl<br>\|<br>NHCH(CH$_2$)$_2$-2 or 3-(1-methylindolyl) |
| H | 1 | Ph | COO-t-Butyl<br>\|<br>NHCH(CH$_2$)$_2$-2 or 3-(1-methylindolyl) |

The invention is further defined by reference to the following preparations and examples, which are intended to be illustrative and not limiting.

All temperatures are in degrees Celsius.

Preparation 1

1,3-Dihydro-3(R)-(3'-indolyl)methyl-5-(2'-fluorophenyl)-2H-1,4-benzodiazepin-2-thione 1,3-Dihydro-3(R)-(3'-indolyl)methyl-5-(2'-fluorophenyl)-2H-1,4-benzodiazepin-2-one (6.98 g, 18.20 mmole) was refluxed with 4.41 g (10.92 mmole) of 2,4-bis-(4-methoxyphenyl)-2,4-dithioxo-1,3,2,4-dithiadiphosphetane in 100 ml of toluene for 1.5 hours. The solvent was removed in vacuo and the residue partitioned between ethyl acetate and 10% sodium hydroxide solution. The organic phase was washed with 10% sodium hydroxide (3×50 ml) and brine, then dried (MgSO$_4$) and rotoevaporated to give an orange oil (10 g). Plug filtration of the crude product through silica gel (100 g) afforded a solid which was recrystallized from ether to afford the analytical sample as an ether solvate. m.p. 147°–148° C.

Pmr confirmed the structure of the title compound.

EXAMPLE 1

2-Phenylamino-3(R)-(3'-indolyl)methyl-5-(2'-fluorophenyl)-2H-1,4-benzodiazepine 2-Methylthio-3(R)-(3'-indolyl)methyl-5-(2'-fluorophenyl)-2H-1,4-benzodiazepine (170 mg, 0.42 mmole) was mixed with 138 μl (3.6 equivalents) of aniline and the whole immersed in a preheated bath at 80° C. After 2 days, the dark reaction mixture was chromatographed on silica gel (hexane-ethyl acetate elution 2:1 v/v) to give the analytical sample as an off-white solid, m.p. 127°.

TLC, HPLC: greater than 98% pure
MS (20 ev): 458 (M+), 366, 329, 130.
Pmr (CDCl$_3$): Confirmed the structure of the title compound.
Elemental Analysis: C$_{30}$H$_{23}$FN$_4$ 0.2H$_2$O. Calc'd: N, 12.12; C, 77.96; H, 5.10. Found: N, 12.22; C, 77.89; H, 4.93.

EXAMPLE 2

2-Methylthio-3(R)-(3'-indolyl)methyl-5-(2'-fluorophenyl)2H-1,4-benzodiazepine Thioamide according to Preparation 1 (2.66 g, 6.66 mmole) was added to a suspension of 40% sodium hydroxide solution (30 ml), 50 ml of toluene, 25 ml of tetrahydrofuran, and 10 ml of water. The reaction mixture was then treated with 1.49 g (0.66 equivalents) of tetra-n-butyl ammonium sulfate. After 5 minutes, 456 μl (1.1 equivalents) of iodomethane was added to the rapidly stirred suspension. The reaction was stirred at room temperature for 15 minutes more, poured into a separatory funnel and the phases separated. The organic phase was washed with water and brine, then dried (MgSO$_4$) and concentrated to yield 2.8 g of the crude product. The analytical sample was obtained via flash column chromatography on silica gel (hexane-ethyl acetate elution, 2:1 v/v). TLC, HPLC: greater than 97.9% pure MS (20 ev): 413 (M+), 284, 130.
Pmr (CDCl$_3$): Spectrum according to theory. S$\underline{CH_3}$ (2.49 ppm)
Elemental Analysis: C$_{25}$H$_{20}$FN$_3$OS 0.3H$_2$O. Calc'd: N, 10.03; C, 71.67; H, 4.95. Found: N, 9.84; C, 71.74; H, 4.66.

EXAMPLE 3

2-Amino-3(R)-(3'-indolyl)methyl-5-(2'-fluorophenyl)-2H1,4-benzodiazepine

Thioamide according to Preparation 1 (170 mg, 0.43 mmole) was dissolved in warm methanol (6 ml). Concentrated ammonium hydroxide solution (58%) (2 ml) was added followed by 117 mg (0.43 mmole) of mercuric chloride. The reaction mixture was stirred vigorously for 3 hours, cooled and filtered through Celite. The filtrate was concentrated to dryness and the resulting white solid (200 mg) chromatographed on silica gel (chloroform-ethanol-ammonia, 90:10:1 v/v) to give the analytical product (120 mg).

TLC, HPLC: greater than 98% pure
MS (20 ev): 382 (M+), 253, 211, 130.
Pmr (CDCl$_3$): Confirmed the structure of the title compound.
$^{19}$F nmr (CD$_3$OD): 113 ppm
Elemental Analysis: C$_{24}$H$_{19}$FN$_4$ 0.25H$_2$O. Calc'd: N, 14.48; C, 74.49; H, 5.07. Found: N, 14.72; C, 74.41; H, 4.92.

EXAMPLE 4

2-Methylamino-3(R)-(3'-indolyl)methyl-5-(2'-fluorophenyl)-2H-1,4-benzodiazepine This compound was prepared according to Example 3 using 2 g (5 mmole) of thioamide according to Preparation 1, 2 g (7.4 mmole) of mercuric chloride, and 20 equivalents of methylamine in 30 ml of dry tetrahydrofuran. Yield of crude product=2.05 g as a white powder. TLC, HPLC: greater than 95% pure MS (14 ev): 396 (M+), 277, 211.
Pmr (CDCl$_3$): Confirmed the structure of the title compound; N-methyl protons resonate as a doublet at 2.94 ppm.
Elemental Analysis: C$_{25}$H$_{21}$FN$_4$ 0.2 CHCl$_3$. Calc'd: N, 13.33; C, 72.00; H, 5.08. Found: N, 13.11; C, 72.08; H, 5.26.

EXAMPLE 5

2-Ethoxycarbonylmethylamino-3(R)-(3'-indolyl)methyl-5-(2'-fluorophenyl)-2H-1,4-benzodiazepine This compound was prepared according to Example 3 using 300 mg (0.75 mmole) of thioamide according to Preparation 1, 310 mg (1.13 mmole) of mercuric chloride and four equivalents of glycine ethyl ester in 25 ml of dry tetrahydrofuran. Work-up afforded 400 mg of crude product. The analytical sample was obtained via silica gel chromatography (chloroform-methanol 99:1 v/v).

HPLC, TLC: greater than 92% pure.
Pmr (CDCl$_3$): Confirmed the structure of the title compound.
MS (14 ev): 468 (M+), 422, 339.
Elemental Analysis: C$_{28}$H$_{25}$FN$_4$O$_2$ 0.1 CHCl$_3$. Calc'd: N, 11.66; C, 70.24; H, 5.26. Found: N, 11.39; C, 70.46; H, 5.43.

EXAMPLE 6

2-Cyanoamino-3(R)-(3'-indolyl)methyl-5-(2'-fluorophenyl)-2H-1,4-benzodiazepine This compound was prepared according to Example 3 using 300 mg (0.75 mmole) of thioamide according to Preparation 1, 310 mg (1.2 mmole) of mercuric chloride and 3 equivalents of cyanamide in 20 ml of dry tetrahydrofuran. Yield of crude product was 330 mg. Chromatography on silica gel using 1% methanol in chloroform gave the analytical sample. TLC, HPLC: greater than 96% pure.

MS (14 ev): 407 (M+), 378, 278.
Pmr (CDCl$_3$): Confirmed the structure of the title compound.
Elemental Analysis: C$_{25}$H$_{18}$FN$_5$ 1.05CHCl$_3$. Calc'd: N, 13.14; C, 58.71: H, 3.60. Found: N, 13.11; C, 58.59; H, 3.66.

EXAMPLE 7

2-Propylamino-3(R)-(3'-indolyl)methyl-5-(2-fluorophenyl)-2H-1,4-benzodiazepine 1,3-Dihydro-3(R)-(3'-indolyl)methyl-5-(2-fluorophenyl)-2H-1,4-benzodiazepin-2-thione (350 mg, 0.88 mmole) was dissolved in 20 ml of dry methanol. The solution was warmed to 50° C. and treated in succession with n-propylamine (1 ml, 12.2 mmole) and mercuric chloride (357 mg, 1.31 mmole). The reaction mixture was stirred at 50° C. for two hours during the course of which a black precipitate was deposited. The reaction mixture was filtered, concentrated in vacuo and the residue dissolved in ethyl acetate. The organic phase was washed with sodium thiosulfate solution (2×30 ml) and brine, then dried (MgSO4) and concentrated to yield 400 mg of crude product. Silica gel chromatography of the crude product (hexane-acetone elution, 3:1 v/v) afforded the analytical sample.

TLC, HPLC: greater than 99.5% pure.
Pmr (CDCl3): according to theory.
MS (14 ev): 424 (M+).
Elemental Analysis: $C_{27}H_{25}FN_4 \cdot 0.2H_2O$ Calc'd: N, 13.08; C, 75.74; H, 5.98. Found: N, 12.56; C, 75.93; H, 6.26.

EXAMPLE 8

2-Carboxymethylamino-3(R)-(3'-indolyl)methyl-5-(2'-fluorophenyl)-2H-1,4-benzodiazepine To a solution of 1,3-dihydro-3(R)-(3-indolyl)methyl-5-(2-fluorophenyl)-2H-1,4-benzodiazepin-2-thione (300 mg, 0.75 mmole) in 15 ml of dry tetrahydrofuran was added mercuric chloride (310 mg, 1.13 mmole) and glycine tert-butyl ester hydrochloride. The pH of the resulting suspension was adjusted to 8.5 with triethylamine and the reaction mixture was then heated at 55° C. for 2 hours. The reaction was cooled, filtered through a Celite pad and concentrated. The residual semi-solid was dissolved in ethyl acetate (150 ml) and washed with sodium thiosulfate solution (2×50 ml) and brine. The dried ((MgSO4) organic phase was concentrated to yield 500 mg of crude product which was flash chromatographed on silica gel (hexane-ethyl acetate elution, 1:1 v/v) to remove polar biproducts. A portion of the purified intermediate ester (220 mg) was dissolved in 50 ml of ethyl acetate, cooled to 0° C. and treated with a continuous stream of hydrogen chloride gas for 30 minutes. The reaction mixture was then allowed to warm to room temperature and stand for 5 hours. Excess reagent and solvent were removed in vacuo to yield 200 mg of an orange-brown powder. The analytical material was obtained via silica gel chromatography (chloroform-methanol-acetic acid elution, 90:10:1 then 85:15:1.5 v/v) as an off-white powder (120 mg).

HPLC: greater than 96% pure.
Pmr (CD3OD): according to theory.
MS (14 ev): 422 (M+—H2O), 293, 277, 264, 246.
Elemental Analysis: $C_{26}H_{21}FN_4O_2 \cdot 0.8CHCl_3 \cdot 0.8HOAc$. Calc'd: N, 9.59; C, 58.40; H, 4.31.
Found: N, 9.50; C, 58.31; H, 4.49.

Preparation 2

1,3-Dihydro-3-[(4-chlorophenyl)aminocarbonyl]amino-5-phenyl-2H-1,4-benzodiazepin-2-thione 1,3-Dihydro-3-amino-5-phenyl-2H-1,4-benzodiazepin-2-thione (1.5 mmole) and 4-chlorophenylisocyanate (1.5 mmole) were combined in 40 mL of dry tetrahydrofuran at 0° C. The reaction mixture was warmed to room temperature over a 1 hour period and diluted with 20 mL of tetrahydrofuran. The reaction mixture was filtered and concentrated under reduced pressure. The residual material was chromatographed on silica gel (96:4:0.4 chloroform-methanol-concentrated ammonium hydroxide) to give the title compound analytically pure after trituration with ether/petroleum ether: the 1HNMR spectrum is consistent with the structure of the title compound.

Preparation 3

1,3-Dihydro-3-[(3-methylphenyl)aminocarbonyl]amino-5-phenyl-2H-1,4-benzodiazepin-2-thione 1,3-Dihydro-3-amino-5-phenyl-2H-1,4-benzodiazepin-2-thione (400 mg, 1.5 mmole) and m-tolylisocyanate (194 μL, 1.5 mmole) were combined in 40 mL of dry tetrahydrofuran at 0° C. The reaction mixture was warmed to room temperature over a 1 hour period and diluted with 20 mL of tetrahydrofuran. The reaction mixture was filtered and concentrated under reduced pressure. The residual material was chromatographed on silica gel (96:4:0.4 chloroform-methanol-concentrated ammonium hydroxide) to give 480 mg of the title compound analytically pure after trituration with ether/petroleum ether:
m.p. 164° C.;
FAB MS=401 (M+ +1);
the 1HNMR spectrum is consistent with the structure of the title compound.

EXAMPLE 9

N-[3-(((4-Chlorophenyl)aminocarbonyl)amino)-5-phenyl-3H-1,4-benzodiazepin-2-yl]-glycine Thioamide according to preparation 2 (80 mg, 0.20 mmole) was dissolved in dry tetrahydrofuran (5 ml). To this solution was added glycine t-butylester hydrochloride (134 mg, 0.80 mmole) and mercuric chloride (80 mg, 0.3 mmole). The pH of the reaction mixture was adjusted to approximately 8.5 with triethylamine and the reaction mixture was stirred at 55° C. for 3 hours. The reaction mixture was cooled, filtered and concentrated. The residue was partitioned between ethyl acetate and sodium thiosulfate solution. The organic phase was washed with brine and dried (Na2SO4). The dry ethyl acetate solution was then cooled to 0° C. and treated with a continuous stream of HCl gas for 30 minutes. The flask was stoppered and after 2 hours at room temperature, solvent and HCl gas were removed in vacuo. The residual solid was chromatographed on silica gel (CHCl3—CH3OH—AcOH elution, 90:10:1 v/v) to afford a solid which was triturated with methanol to give 26 mg of the analytical product: mp 186° C. (gas evolution).

TLC, HPLC: 98.9% pure
MS (FAB): 462 (M+H)
PMR (DMSO-d6): Confirms the structure assignment
Elemental Analysis: $C_{24}H_{20}ClN_5O_3 \cdot \frac{1}{4}H_2O$. Calc'd: C, 61.80; H, 4.43; N, 15.02. Found: C, 61.84; H, 4.59; N, 14.75.

EXAMPLE 10

N-[3-(((4-Chlorophenyl)aminocarbonyl)amino)-5-phenyl-3H-1,4-benzodiazepin-2-yl]-glycine ethyl ester Thioamide according to preparation 2 (100 mg, 0.25 mmole) was combined with glycine ethyl ester hydrochloride (140 mg, 1 mmole) and mercuric chloride (100 mg, 0.38 mmole). The pH of the reaction mixture was adjusted to approximately 8.5 with triethylamine. The reaction mixture was protected from moisture and cooled, filtered and the filtrate was concentrated to dryness. The residual solid was partitioned between ethyl acetate and sodium thiosulfate solution. The organic phase was washed with brine, dried (Na2SO4) and concentrated to give an oil. Preparative chromatography on silica gel (CHCl3—CH3OH—NH4OH elution, 97:3:0.3 v/v) afforded 80 mg of the analytical product; recrystallization from ether gave shimmering crystals: mp 164°–165° C.

TLC, HPLC: Greater than 99.9% pure.

MS (FAB): 490 (M+H)

PMR (CDCl$_3$): Confirms structure assignment of product and ether solvate.

Elemental Analysis: $C_{26}H_{24}ClN_5O_3 \cdot \frac{1}{2}C_4H_{10}O$. Calc'd: C, 63.81; H, 5.55; N, 13.29. Found: C, 63.76; H, 5.39; N, 13.12.

EXAMPLE 11

1-[[(3-((3-Methylphenylaminocarbonyl)amino)-5-phenyl-3H-1,4-benzodiazepin-2-yl)amino]acetyl]-pyrrolidine 1,3-Dihydro-3-[(3-methylphenyl)aminocarbonyl]amino-5-phenyl-2H-1,4-benzodiazepin-2-thione (75 mg, 0.19 mmole), obtained according to Preparation 3, was combined with 125 mg (0.76 mmole) of glycine pyrrolidinylamide hydrochloride and mercuric chloride (79 mg, 0.29 mmole) in 10 mL of dry tetrahydrofuran. The pH of the reaction mixture was adjusted to approximately 8.5 with triethylamine and heated to 55° C. (bath temperature) for one hour. The reaction mixture was cooled, filtered, and the filtrate was concentrated to dryness. The residual oil was purified by preparative thick layer chromatography on silica gel (98:2:0.2 chloroform-methanol-concentrated ammonium hydroxide) to yield the title compound. Recrystallization from ether-methanol (10:1) afforded white, star-like crystals: m.p. 229° C. (d).

HPLC=99.7% pure at 214 nm.

NMR (DMSO-D$_6$): Consistent with structure assignment and confirms presence of solvent.

FAB MS: 495 (M+ +1).

Analysis for $C_{29}H_{30}N_6O_2 \cdot 0.25$ H$_2$O Calculated: C, 69.78; H, 1.16; N, 16.84. Found: C, 69.66; H, 6.33; N, 16.74.

EXAMPLE 12

1-Methyl-4-[[(3-((((3-methylphenyl)amino)carbonyl)amino)-5-phenyl-3H-1,4-benzodiazepin-2-yl)amino]acetyl]-piperazine 1,3-Dihydro-3-[(3-methylphenyl)aminocarbonyl]amino-5-phenyl-2H-1,4-benzodiazepin-2-thione (150 mg, 0.37 mmole), obtained according to Preparation 3, was combined with 340 mg (1.48 mmole) of glycine 1-methylpiperazinyl amide hydrochloride and mercuric chloride (152 mg, 0.56 mmole) in 10 mL of dry tetrahydrofuran. The pH of the reaction mixture was adjusted to approximately 8.5 with triethylamine and heated to 55° C. (bath temperature) for 2 hours. The reaction mixture was cooled, filtered, and the filtrate was concentrated to dryness. The residual oil was purified by preparative thick layer chromatography on silica gel (90:10:1 chloroform-methanol-concentrated ammonium hydroxide) to yield the title compound. Trituration with ether afforded white crystals: m.p. 153°–155° C. (d).

HPLC>93.7% pure at 214 nm.

NMR (DMSO-D$_6$): Consistent with structure assignment and confirms presence of solvent.

FAB MS: 524 (M+ +1).

Analysis for $C_{30}H_{30}N_7O_2 \cdot 0.5$ H$_2$O. Calculated: C, 67.64; H, 6.43; N, 18.40. Found: C, 67.67; H, 6.23; N, 18.06.

EXAMPLE 13

N-[2-[((3-Diethylamino)propyl)amino]-5-phenyl-3H-1,4-benzodiazepin-3-yl]-N'-[3-methylphenyl]-urea 1,3-Dihydro-3-[(3-methylphenyl)aminocarbonyl]amino-5-phenyl-2H-1,4-benzodiazepin-2-thione (53 mg, 0.13 mmole), obtained according to Preparation 3, was combined with 68 mg (0.52 mmole) of glycine 1-methylpiperazinyl amide hydrochloride and mercuric chloride (54 mg, 0.20 mmole) in 3 mL of dry tetrahydrofuran. The pH of the reaction mixture was adjusted to approximately 8.5 with triethylamine and heated to 55° C. (bath temperature) for 2.5 hours. The reaction mixture was cooled, filtered, and the filtrate was concentrated to dryness. The residual oil was purified by preparative thick layer chromatography on silica gel (96:4:0.4 chloroform-methanol-concentrated ammonium hydroxide). Trituration with ether/petroleum ether afforded the title compound as a white solid:

m.p. 158°–159° C.

HPLC>99% pure at 214 nm.

NMR (DMSO-D$_6$): Consistent with structure assignment and confirms presence of solvent.

FAB MS: 497 (M+ +1).

Analysis for $C_{30}H_{36}N_6O \cdot 0.4$ H$_2$O. Calculated: C, 71.50; H, 7.36; N, 16.68. Found: C, 71.42; H, 7.18; N, 16.87.

EXAMPLE 14

N-[3-Methylphenyl]-N'-[2-((3-(2-oxo)pyrrolidinyl)propyl)amino-5-phenyl-3H-1,4-benzodiazepin-3-yl]-urea 1,3-Dihydro-3-[(3-methylphenyl)aminocarbonyl]amino-5-phenyl-2H-1,4-benzodiazepin-2-thione (75 mg, 0.19 mmole), obtained according to Preparation 3, was combined with 106 μL (0.76 mmole) of 1-(3-aminopropyl) 2-pyrrolidinone and mercuric chloride (79 mg, 0.29 mmole) in 6 mL of dry tetrahydrofuran. The pH of the reaction mixture was approximately 9. The reaction mixture was cooled, filtered, and the filtrate was concentrated to dryness. The residual oil was purified by preparative thick layer chromatography on silica gel (97:3:0.3 chloroform-methanol-concentrated ammonium hydroxide). Trituration with ether/petroleum ether afforded 138 mg of the title compound as a white solid:

m.p. 179°–180° C.

HPLC>99% pure at 214 nm.

NMR (DMSO-D$_6$): Consistent with structure assignment and confirms presence of solvent.

FAB MS: 509 (M+ +1).

Analysis for $C_{30}H_{32}N_6O_2$. Calculated: C, 70.56; H, 6.39; N, 16.24. Found: C, 70.47; H, 6.70; N, 16.30.

What is claimed is:

1. A method of treating panic disorder or anxiety disorder in a mammal which comprises administering to said mammal a therapeutically effective amount of a compound of the formula:

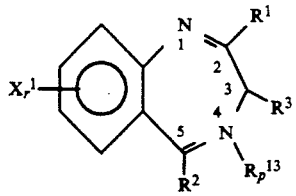 I wherein

R¹ is —NR¹⁶R¹⁷;

R² is H, loweralkyl, substituted or unsubstituted phenyl (wherein the substituents are 1 or 2 of halo, loweralkyl, loweralkoxy, loweralkylthio, carboxyl, carboxyloweralkyl, nitro, —CF₃, or hydroxy), 2-, 3-, 4-pyridyl, —X¹²COOR⁶,

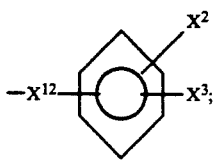

R³ is —X¹¹R⁷,

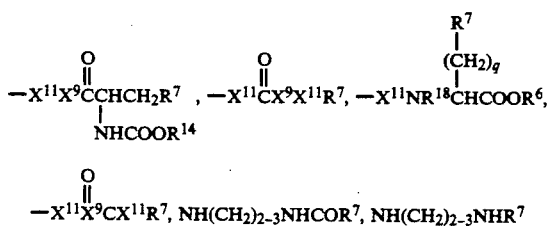

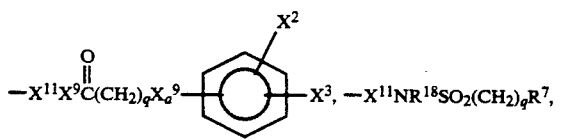

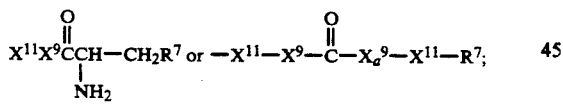

R⁴ and R⁵ are independently R⁶ or in combination with the N of the NR⁴R⁵ group form an unsubstituted or mono or disubstituted, saturated or unsaturated, 4-7 membered heterocyclic ring, or benzofused 4-7 membered heterocyclic ring or said heterocyclic ring or said benzofused heterocyclic ring which further comprises a second heteroatom selected from O and NCH₃ and the substituent(s) is/are independently selected from C₁₋₄alkyl;

R⁶ is H, loweralkyl, cycloloweralkyl, substituted or unsubstituted phenyl, or substituted or unsubstituted phenylloweralkyl (wherein the substituents are 1 or 2 of halo, loweralkyl, loweralkoxy, nitro, or CF₃);

R⁷ is α- or β-naphthyl, substituted or unsubstituted phenyl (wherein the substituents are 1 to 2 of halo, —NO₂, —OH, —X¹¹—NR⁴R⁵, loweralkyl, loweralkoxy, CF₃), loweralkylthio, cyano, phenyl, acetylamino, acetoxy, SCF₃, C≡CH, CH₂SCF₃, OCHF₂, SH or thio-phenyl) 2-, 3-, 4-pyridyl 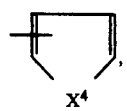,

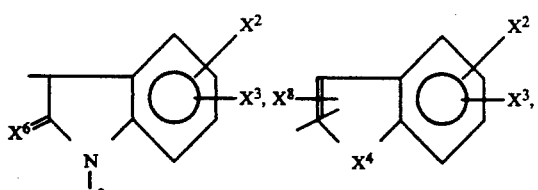

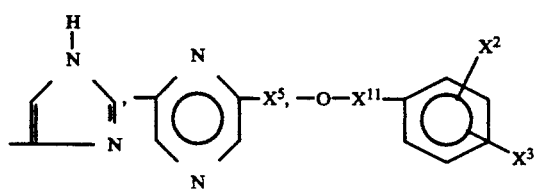

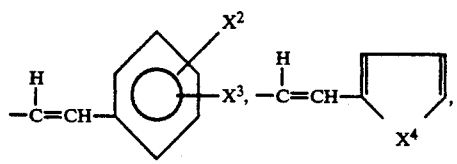

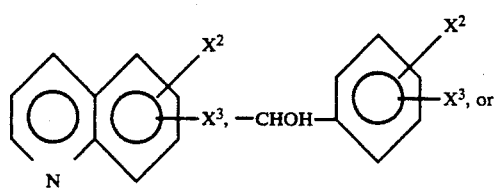

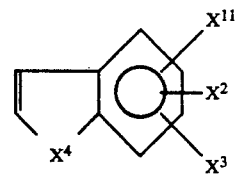

with the proviso that q is not 0 in

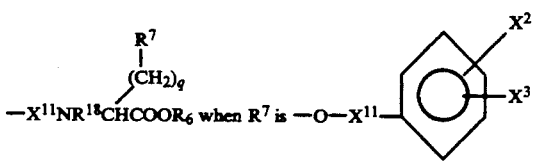

R⁸ is H, loweralkyl, cycloloweralkyl, —X¹²CONH₂, —X¹²COOR⁶, —X¹¹-cycloloweralkyl, —X¹²NR⁴R⁵,

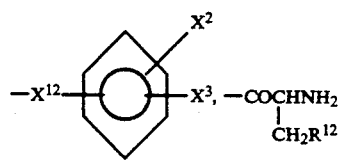

-continued

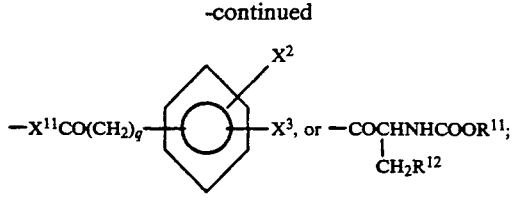

$R^{11}$ and $R^{12}$ are independently loweralkyl or cycloloweralkyl;

$R^{13}$ is O;

$R^{14}$ is loweralkyl or phenylloweralkyl;

$R^{16}$ and $R^{17}$ are, when separate, independently H, loweralkyl, lower alkenyl, —$X^{11}$cycloloweralkyl, —$X^{12}$—$NR^4R^5$, $X^{12}CONR^4R^5$, —$X^{12}C\equiv N$,

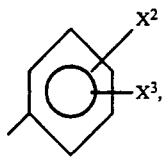

—$X^{12}COOR^6$, or —CN; or, when joined, form with N, a heterocycle

wherein n' is 2–6;

$R^{18}$ is H or loweralkyl;

p is 0 or 1;

q is 0–4;

r is 1 or 2;

$X^1$ is H, —$NO_2$, $CF_3$ CN, OH, loweralkyl, halo, loweralkylthio, loweralkoxy, —$X^{11}COOR^6$ or —$X^{11}NR^4R^5$;

$X^2$ and $X^3$ are independently H, —OH, —$NO_2$, halo, loweralkylthio, loweralkyl or loweralkoxy;

$X^4$ is S, O, $CH_2$ or $NR^8$;

$X^5$ is H, $CF_3$, CN, $COOR^6$, $NO_2$, or halo;

$X^6$ O or HH;

$X^8$ is H or loweralkyl;

$X^9$ and $X^9{}_a$ are independently $NR^{18}$, O;

$X^{11}$ is absent or $C_{1-4}$ linear or branched alkylidene;

$X^{12}$ is $C_{1-4}$ linear or branched alkylidene;

or a pharmaceutically acceptable salt thereof, and a pharmaceutically acceptable carrier.

2. The method according to claim 1, wherein the therapeutically effective amount of the compound of Formula I is from about 0.005 mg/kg to about 50 mg/kg of body weight, administered to said mammal in a single or divided dose.

3. The method according to claim 1, wherein said mammal is a human.

* * * * *